(12) United States Patent
Leng et al.

(10) Patent No.: US 12,234,504 B1
(45) Date of Patent: Feb. 25, 2025

(54) HIGH THROUGHPUT SCREENING ASSAY TO IDENTIFY DNA TOPOISOMERASE INHIBITORS

(71) Applicants: Fenfei Leng, Palmetto Bay, FL (US); Matthew Dias, Miami, FL (US)

(72) Inventors: Fenfei Leng, Palmetto Bay, FL (US); Matthew Dias, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 18/903,582

(22) Filed: Oct. 1, 2024

Related U.S. Application Data

(60) Provisional application No. 63/544,373, filed on Oct. 16, 2023.

(51) Int. Cl.
| | |
|---|---|
| C12Q 1/682 | (2018.01) |
| C12Q 1/37 | (2006.01) |
| C12Q 1/44 | (2006.01) |
| C12Q 1/533 | (2006.01) |
| C12Q 1/6832 | (2018.01) |

(52) U.S. Cl.
CPC ............. *C12Q 1/682* (2013.01); *C12Q 1/37* (2013.01); *C12Q 1/44* (2013.01); *C12Q 1/533* (2013.01); *C12Q 1/6832* (2013.01)

(58) Field of Classification Search
CPC .............................. C12Q 1/686; C12Q 1/6806
See application file for complete search history.

(56) References Cited

U.S. PATENT DOCUMENTS

2014/0357498 A1* 12/2014 Felix .................... C12Q 1/6886
435/6.12

OTHER PUBLICATIONS

Deng et al.., "A T5 Exonuclease-Based Assay for DNA Topoisomerases and DNA Intercalators," ACS Omega, vol. 6, pp. 12205-12212. (Year: 2021).*

* cited by examiner

*Primary Examiner* — Young J Kim
(74) *Attorney, Agent, or Firm* — SALIWANCHIK, LLOYD & EISENSCHENK

(57) ABSTRACT

The subject invention provides a novel fluorescence-based, T5 exonuclease-amplified DNA cleavage assay for gyrase poisoning inhibitor discovery. According to the assay, multiple gyrase molecules can simultaneously bind to a plasmid DNA molecule to form multiple gyrase-DNA cleavage complexes on the same plasmid. These gyrase-DNA cleavage complexes, greatly stabilized by a gyrase poisoning inhibitor, and can be trapped by a detergent such as sarkosyl. Digestion of gyrase by proteinase K results in the production of small DNA fragments, which can be digested by T5 exonuclease. This fluorescence-based DNA cleavage HTS assay is also suitable for screening large compound libraries to identify inhibitors against DNA topoisomerases, including human DNA topoisomerase IIα.

18 Claims, 16 Drawing Sheets

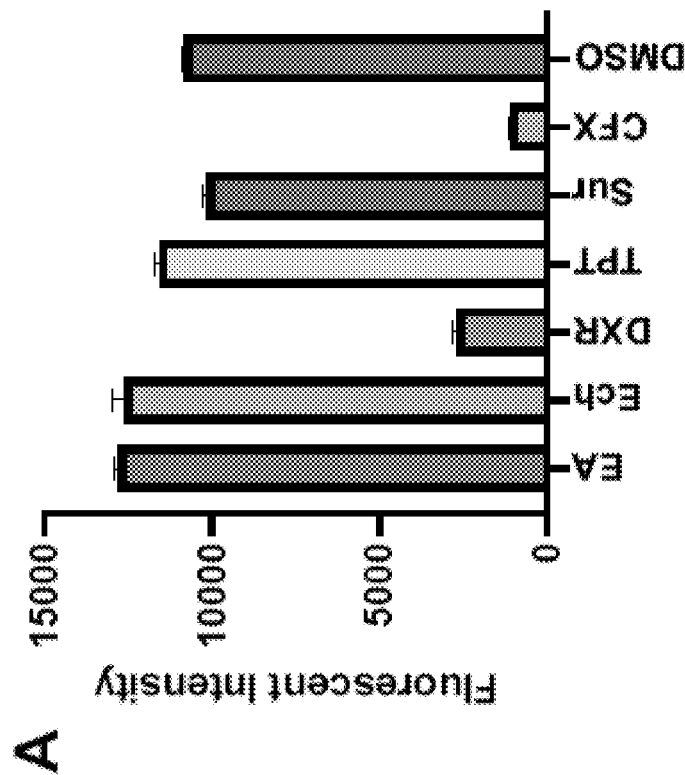
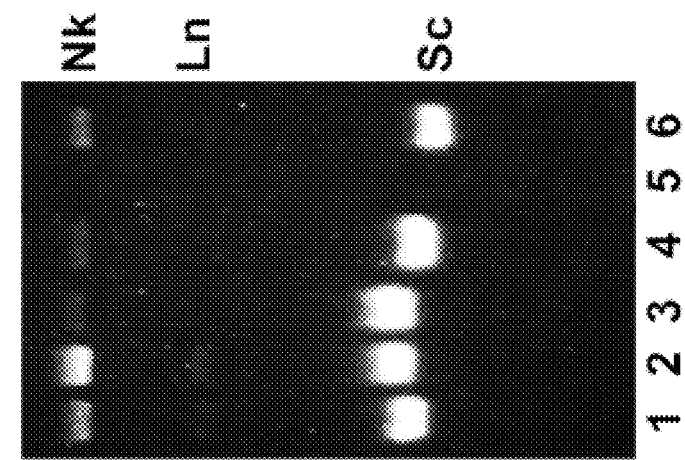
FIG. 7A
FIG. 7B

HIGH THROUGHPUT SCREENING ASSAY TO IDENTIFY DNA TOPOISOMERASE INHIBITORS

CROSS-REFERENCE TO RELATED APPLICATION

This application claims the benefit of U.S. Provisional Application Ser. No. 63/544,373, filed Oct. 16, 2023, the disclosure of which is hereby incorporated by reference in its entirety, including all figures, tables, and drawings.

BACKGROUND

Bacterial DNA gyrase, a type IIA DNA topoisomerase, is an essential enzyme for bacteria. It contains two distinct subunits, GyrA and GyrB that form an active tetrameric $A_2B_2$ complex. GyrA carries an active tyrosine residue used in DNA cleavage and re-ligation reactions for DNA supercoiling activity. GyrB contains an ATP-binding site that is also required for DNA supercoiling. The absence of DNA gyrase in human cells makes this enzyme a highly promising and valuable target for the discovery and development of novel antibiotics. Presently, there are two main classes of gyrase inhibitors: catalytic and poisoning inhibitors. Catalytic inhibitors, such as novobiocin, primarily target the ATP binding site of GyrB, inhibiting the gyrase's supercoiling activity. Unfortunately, novobiocin was withdrawn from the US market due to an unfavorable efficacy and safety profile. Several pharmaceutical companies have also synthesized a vast array of compounds with anti-GyrB ATPase and anti-bacterial activities over the past three decades. However, no synthetic GyrB inhibitors has been successfully developed into antibiotics yet.

Gyrase poisoning inhibitors/gyrase poisons, such as fluoroquinolones (FQs), target the active tyrosine site of GyrA through stabilizing the gyrase-DNA cleavage-complex intermediates during DNA supercoiling cycle. This gyrase poisoning mechanism makes FQs among the most effective antibiotics. Unfortunately, bacterial resistance to FQs has emerged and makes the development of new, more effective antibiotics a great urgency. Additionally, FQs have been explored extensively. The limits and potential of FQs likely have been reached. Furthermore, the use of FQs is associated with serious side effects, including tendonitis and tendon rupture, peripheral neuropathy, hyperglycemia, and aortic complications. Consequently, FDA has issued multiple warnings for the use of FQs and implemented black box warnings on all FQs.

In light of these challenges, there is an evident need to discover novel types of compounds targeting bacterial DNA gyrases to effectively treat bacterial infections. Examples of this ongoing effort include novel bacterial topoisomerase inhibitors (NTBIs), such as gepotidacin and zoliflodacin. These NTBIs, currently under phase 3 clinical trials for the treatment of gonorrhea, also poison gyrase, albeit targeting a different site on gyrase-DNA complexes. These new gyrase poisoning inhibitors offer great promise to fight "superbugs" that are resistant to almost all antibiotics and avoid facing a future pandemic of untreatable bacterial infections.

An effective approach for discovering new DNA gyrase poisoning inhibitors/gyrase poisons is through high throughput screening (HTS) of compound libraries that contain thousands or millions of drug-like compounds. However, there are currently no HTS assays that can identify or discover DNA gyrase poisoning inhibitors/gyrase poisons. Instead, labor-intensive and time-consuming agarose or PAGE gel-based assays are typically used to identify or confirm gyrase poisoning inhibitors. Nevertheless, several HTS assays are available to identify gyrase inhibitors that target the DNA supercoiling activity of gyrase.

For example, a miniaturized, automated ultra-high-throughput screening (uHTS) assay was recently established based on the supercoiling-dependent fluorescence quenching (SDFQ) assay of DNA topoisomerases. The NIH's Molecular Libraries Small Molecule Repository (MLSMR) library, which contains 370,620 compounds, were screened and ~3,000 DNA gyrase inhibitors were identified. Although most of these newly identified gyrase inhibitors are catalytic inhibitors, several are poisoning inhibitors/poisons. This was confirmed by performing agarose-gel based DNA cleavage assays by gyrase. Another HTS assay, a T5 exonuclease (T5E) AT-hairpin-based HTS assay, has also been used to identify gyrase inhibitors. This assay is based on a unique property of T5E that can completely digest supercoiled plasmid pAB1 containing an "AT" hairpin structure and spare relaxed pAB1. This HTS assay can also be converted into a miniaturized, automated uHTS assay for DNA topoisomerases.

In addition to bacterial DNA gyrase, other DNA topoisomerases are also important drug targets because DNA topoisomerases are essential enzymes. Currently, all clinically relevant drugs targeting DNA topoisomerases act as poisoning inhibitors/poisons. For example, doxorubicin and etoposide are poisons to human DNA topoisomerase IIα. Camptothecin and analogs kill cancer cells through poisoning human DNA topoisomerase I. As mentioned above, FQs, such as ciprofloxacin, are poisoning inhibitors/poisons against bacterial DNA gyrase and topoisomerase IV. A recent study demonstrated the effectiveness of cyanotriazoles as DNA topoisomerase II poisoning inhibitors/poisons, specifically capable of selectively eliminating trypanosome parasites responsible for causing Chagas disease and African sleeping sickness. These DNA topoisomerase II poisoning inhibitors/poisons hold tremendous promise as potential therapeutics for the treatment of Chagas disease. Future efforts should focus on discovering poisoning inhibitors/poisons of DNA topoisomerases including DNA gyrase poisoning inhibitors/poisons.

Thus, there is a need to develop novel assays for discovering bacterial DNA gyrase poisons, which may be used as therapeutics for treating diseases such as bacterial infections.

BRIEF DESCRIPTION OF THE INVENTION

The subject invention provides a novel fluorescence-based, T5 exonuclease-amplified DNA cleavage assay for discovering bacterial DNA gyrase poisoning inhibitors/poisons. This assay can be implemented as an HTS assay to discover new DNA gyrase inhibitors/poisons by screening compound libraries that contain thousands or millions of compounds.

In one embodiment, the subject invention provides an assay based on the observation showing that multiple gyrase molecules can simultaneously bind to a plasmid DNA molecule to form multiple gyrase-DNA cleavage complexes on the same plasmid. These gyrase-DNA cleavage complexes, greatly stabilized by a gyrase poisoning inhibitor/poison, can be trapped by sarkosyl. Digestion of gyrase by proteinase K results in the production of small DNA fragments. T5 exonuclease, which selectively digests linear and nicked DNA, can be used to completely digest the fragmented linear DNA molecules and, therefore, "amplify" the fluorescence signal of the DNA cleavage products after, for example, SYBR™ Green staining.

Advantageously, this fluorescence-based DNA cleavage HTS assay is suitable for screening large compound libraries containing many chemical compounds. Analogous assays can be used to identify inhibitors against other DNA topoisomerases, including human DNA topoisomerase IIα.

The subject invention also provides a fluorescence-based, T5 exonuclease-amplified DNA cleavage assay for DNA topoisomerases inhibitor discovery.

In one embodiment, the subject invention provides a method for identifying an inhibitor targeting a DNA topoisomerase in a sample, the method comprising adding a circular double-stranded plasmid to the sample; adding the DNA topoisomerase; adding a detergent (e.g., SDS, SLES and/or sarkosyl) and a proteinase (e.g., proteinase K or other heat stable, broad-spectrum proteinase, such as a neutral, heat-sensitive serine protease (NHSSP)), adding an exonuclease, such as a T5 exonuclease (T5E); adding a DNA-staining dye; and determining the presence or absence of the inhibitor based on fluorescence in the sample.

In one embodiment, determining the presence or absence of the inhibitor based on the fluorescence in the sample comprises comparing the fluorescence with a control, wherein a lower fluorescence in the sample than the control is indicative of the presence of the inhibitor of the DNA topoisomerase, wherein the control comprises the circular double-stranded plasmid in a supercoiled conformation. In one embodiment, the control does not comprise an inhibitor of the DNA topoisomerase. Because T5E does not digest the circular sc dsDNA, the DNA dye binds such circular sc dsDNA, leading to fluorescence higher in control than in the sample.

In certain embodiments, the method of the subject invention can be used as a high throughput screening (HTS) assay and the sample is a sample in a HTS sample carrier.

In some embodiments, the method further comprises adding ATP in the sample.

In one embodiment, the subject invention provides a method for determining whether a compound is an inhibitor targeting a DNA topoisomerase, the method comprising mixing the compound with a circular double-stranded plasmid and the DNA topoisomerase; adding a detergent (e.g., SLES, SDS and/or sarkosyl) and a proteinase (e.g., proteinase K or other heat stable, broad-spectrum proteinase, such as NHSSP) to the mixture, adding an exonuclease, such as a T5E, to the mixture; adding a DNA-staining dye; and determining whether the compound is an inhibitor targeting the DNA topoisomerase based on fluorescence of the mixture.

In one embodiment, determining whether the compound is an inhibitor based on the fluorescence of the mixture comprises comparing the fluorescence with a control, wherein a lower fluorescence in the mixture than the control indicates that the compound is an inhibitor of the DNA topoisomerase, wherein a higher or comparable fluorescence in the mixture than the control indicates that the compound is not an inhibitor of the DNA topoisomerase, wherein the control comprises the circular double-stranded plasmid in a supercoiled conformation.

In certain embodiments, the DNA topoisomerase is selected from type II DNA topoisomerases such as human DNA topoisomerase II, or DNA gyrase.

In specific embodiments, the circular double-stranded plasmid has the ability to interconvert between a relaxed (rx) configuration and a supercoiled (sc) configuration.

In specific embodiments, the DNA-staining dye is Hoechest 33258, SYBR™ gold, ethidium bromide, EthD-1 (known as ethidium homodimer-1, or 5-ethyl-6-phenylphenanthridin-5-ium-3,8-diamine homodimer-1), or SYBR™ green.

In some embodiments, the method further comprises adding ATP in the mixture.

BRIEF DESCRIPTION OF DRAWINGS

FIGS. 7A-7C. The fluorescence-based, T5 exonuclease-amplified DNA gyrase cleavage assays for ethacridine (EA), echinomycin (Ech), doxorubicin (DXR), topotecan (TPT), and suramin (Sur) at 20 μM were formed as described in Materials and Methods. (A) Fluorescence intensity was measured using a Biotek microplate reader with λex of 497 nm and λem of 525 nm. (B) 1% agarose gels containing 0.5 μg/mL of EB in 1×TAE for DNA samples before dilution. Lanes 1-5 are DNA samples from assays containing ethacridine, echinomycin, doxorubicin, suramin, an ciprofloxacin, respectively. Lane is the DNA sample from an assay containing 1% DMSO as a negative control. (C) Doxorubicin (DXR) efficiently quenched fluorescence of SYBR™ Green. DXR titration assays were performed in 20 μL of 1×DNA cleavage buffer containing 200 ng of Rx pBR322 and different concentrations of DXR. The DNA samples were diluted 100 times using 1×NEB buffer 4. 1×SYBR™ Green was added to all DNA samples. Fluorescence intensity was measured with λex of 497 nm and λem of 525 nm.

DETAILED DESCRIPTION

Figure 1A:
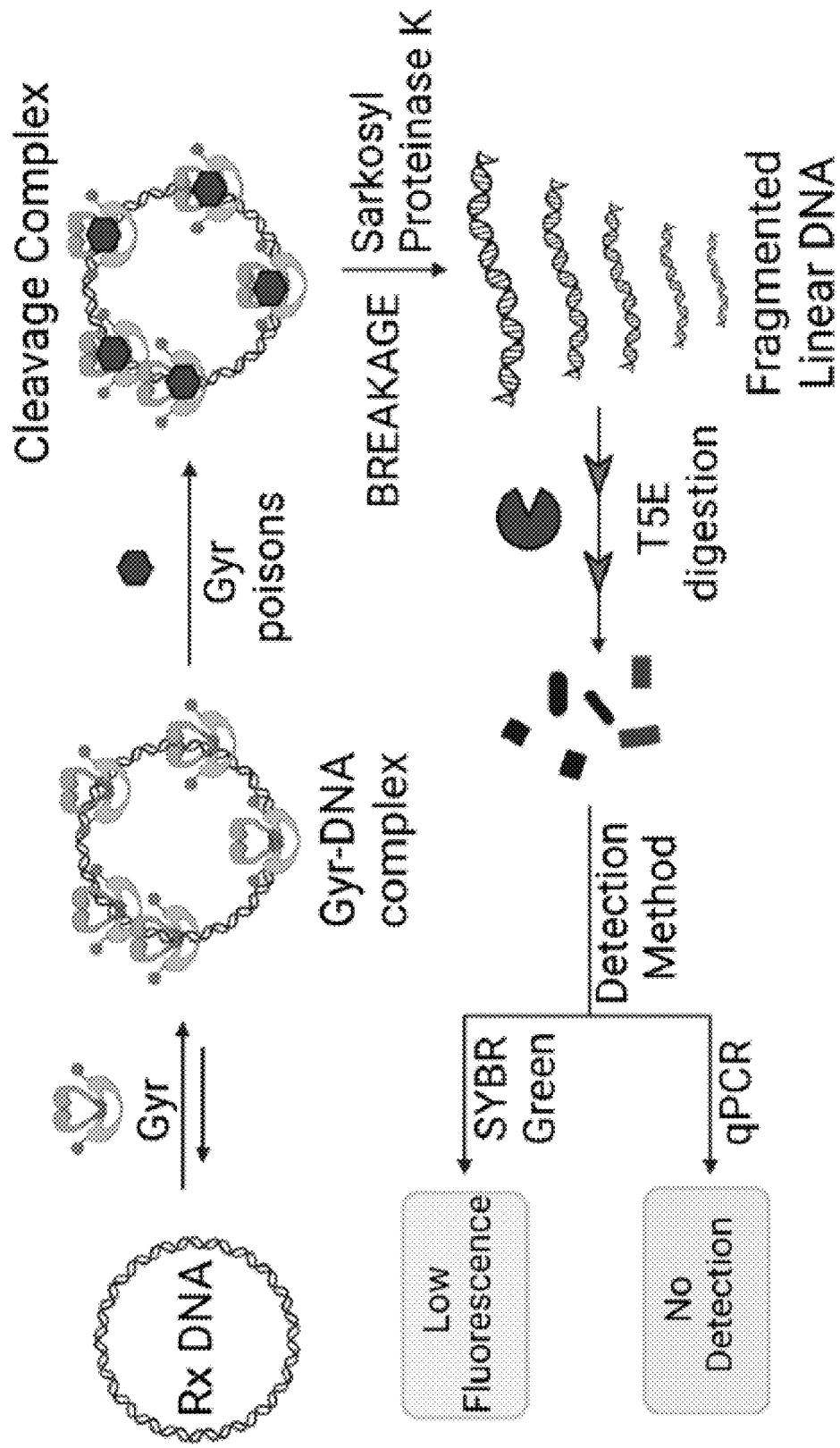
FIGS. 1A-1B. A novel fluorescence-based, T5 exonuclease-amplified DNA cleavage assay for the discovery of bacterial DNA gyrase poisoning inhibitors/poisons. (1A) The principle. (1B) The experimental strategy. This novel unique assay can be implemented as automatic and miniature high throughput screening (HTS) assay to discover/identify bacterial DNA gyrase poisoning inhibitors/poisons by screening compound libraries that contain thousands or millions of compounds.

The subject invention provides sensitive assays and methods for screening or identifying inhibitors that target the DNA topology-affecting enzymes such as DNA topoisomerases (e.g., human DNA topoisomerases, bacterial DNA topoisomerase I, and DNA gyrases), from a compound library comprising a large number of compounds. DNA topoisomerases are targets of anticancer drugs and antibiotics. This technology can be used to identify new topoisomerase inhibitors that can be developed into antibiotics and anticancer drugs.

The subject invention provides a novel fluorescence-based, T5 exonuclease-amplified DNA cleavage assay for discovering bacterial DNA gyrase poisoning inhibitors/poisons. This assay based on the observation showing that multiple gyrase molecules can simultaneously bind to a plasmid DNA molecule to form multiple gyrase-DNA cleavage complexes on the same plasmid. These gyrase-DNA cleavage complexes, greatly stabilized by a gyrase poisoning inhibitor, can be trapped by sarkosyl. Digestion of gyrase by proteinase K results in the production of small DNA fragments. T5 exonuclease, which selectively digests linear and nicked DNA, can be used to completely digest the fragmented linear DNA molecules and, therefore, "amplify" the fluorescence signal of the DNA cleavage products after, for example, SYBR™ Green staining.

Advantageously, this assay can be implemented as an HTS assay to discover new DNA gyrase inhibitors by screening compound libraries that contain thousands or millions of compounds. Analogous assays can be used to identify inhibitors against other DNA topoisomerases, including human DNA topoisomerase IIα.

Gyrase is an enzyme that introduces (-) supercoils into DNA substrates in a reaction that requires the hydrolysis of ATP. Gyrase is also known as DNA topoisomerase II. A gyrase inhibitor refers to a compound that inhibits the activity of gyrase. A gyrase inhibitor can also stabilize the covalent enzyme-DNA complex.

In one embodiment, the assays and methods use a type of unique nucleic acid molecule, preferably, a circular double-stranded (ds) DNA molecule that has the ability to interconvert between a relaxed (rx) configuration and a supercoiled (sc) configuration. Advantageously, such nucleic acid molecules can be used for fast detection of changes in DNA topology due to the ability to convert from the sc conformation to the rx conformation.

In one embodiment, the circular double-stranded DNA molecule is a circular double-stranded plasmid that has the ability to interconvert between a relaxed (rx) configuration and a supercoiled (sc) configuration. The circular double-stranded DNA molecule can also bind to multiple DNA gyrase molecules simultaneously to form a gyrase-plasmid complex, which leads to the formation of multiple gyrase-DNA cleavage complexes on the circular double-stranded DNA molecule.

In certain embodiments, the circular double-stranded plasmid may comprise, for example, about 100 base pairs to 100,000 base pairs, about 500 base pairs to 100,000 base pairs, about 1000 base pairs to 100,000 base pairs, about 1000 base pairs to 50,000 base pairs, about 1000 base pairs to 20,000 base pairs, about 1000 base pairs to 10,000 base pairs, about 1000 base pairs to 5000 base pairs, about 1000 base pairs to 4000 base pairs, about 1000 base pairs to 3000 base pairs, about 1500 base pairs to 3000 base pairs, or about 2000 base pairs to 3000 base pairs.

In a specific embodiment, the circular double-stranded plasmid is pBR322, or pAB1.

In certain embodiments, the circular double-stranded plasmid may comprise at least one DNA endonuclease or exonuclease recognition site that can be recognized by a DNA endonuclease or exonuclease. Subsequently, the circular double-strand plasmid is cleaved or digested by such endonuclease or exonuclease, failing to maintain relaxed and supercoiled configurations.

In one embodiment, the assays and methods of the subject invention take advantage of a unique property of T5E that can initiate nucleotide removal from the 5' termini or at gaps and nicks of linear or circular dsDNA in the 5' to 3' direction. T5E does not degrade sc dsDNAs and relaxed (rx) DNAs. After the T5E digestion of linear and nicked DNAs, the DNA samples can be stained by a DNA-binding dye, e.g., either DNA intercalators or groove binders, to differentiate relaxed/supercoiled DNA and DNA fragments.

In one embodiment, to determine the presence of an inhibitor of a DNA topoisomerase, a sample suspected of containing an inhibitor of the DNA topoisomerase is added to a mixture of the DNA topoisomerase and a circular plasmid. A detergent is then added to trap the enzyme-DNA complex. Then a proteinase is added to the mixture to digest the DNA molecules to DNA fragments. After adding the T5E, the DNA fragments are completely digested leaving the rx and sc circular plasmids intact in their conformation, which can bind to a DNA-staining dye, e.g., SYBR™ green. The fluorescence intensity from the sc DNA samples is significantly higher than that of the digested DNA samples. Quantitative polymerase chain reaction (qPCR) can also be used to as a detection method because if the DNA fragments have been digested by T5E, no signal should be detected in the qPCR detection.

In one embodiment, the subject invention provides a method for screening/identifying inhibitors targeting an enzyme that regulates the DNA topology, e.g., DNA topoisomerase such as DNA gyrase, the method comprises providing a sample suspected of containing an inhibitor of the enzyme, e.g., DNA topoisomerase; mixing the enzyme, e.g., DNA topoisomerase, and a circular dsDNA molecule with the sample, wherein the circular dsDNA molecule has the ability to interconvert between a rx configuration and a sc configuration; adding a detergent, such as SLES, SDS or sarkosyl (sodium lauroyl sarcosinate, SLS); adding a proteinase such as proteinase K or other heat stable, broad-spectrum proteinase, such as NHSSP; adding an exonuclease, e.g., T5E, into the mixture, wherein the exonuclease, e.g., T5E, selectively digests linear and nicked DNA while leaving supercoiled plasmid DNA intact; adding a signal reporter, e.g., a DNA-staining dye; and determining the presence or absence of the inhibitor based on a signal generated from the signal reporter, e.g., fluorescence, in the sample. Because the signal reporter binds to the sc DNAs but not the digested DNAs, high signal from the signal reporter indicates the absence of the inhibitor while low signal indicates the presence of the inhibitor.

Advantageously, this assay is not only capable of detecting gyrase poisons that result in double-stranded DNA breaks but also identify gyrase poisons that lead to single-stranded DNA breaks, such as NTBIs (e.g., gepotidacin).

In one embodiment, the method may further comprise determining and/or quantifying the signal from the reporter in the sample mixture. The signal can be determined or quantified through, for example, an optical measurement, e.g., fluorescent or luminescent detection, colorimetry, and light scatter (turbidity). In one embodiment, other methods known in the art may be used for quantifying the fluorescence in the sample, e.g., plate readers.

In one embodiment, the subject invention provides a method for identifying an inhibitor targeting a DNA topoisomerase in a sample, the method comprising adding a circular double-stranded plasmid to the sample; adding the DNA topoisomerase; adding a detergent (e.g., SLES, SDS and/or sarkosyl) and a proteinase (e.g., proteinase K or other heat stable, broad-spectrum proteinase, such as NHSSP), adding an exonuclease, such as a T5 exonuclease (T5E); adding a DNA-staining dye; and determining the presence or absence of the inhibitor based on fluorescence in the sample.

In one embodiment, the subject invention provides a method for determining the presence of an inhibitor targeting DNA gyrase in a sample, the method comprising providing the sample suspected of containing an inhibitor of the DNA gyrase; adding a circular double-stranded plasmid that has the ability to interconvert between a rx configuration and a sc configuration upon supercoiling of the circular double-stranded plasmid; adding the DNA gyrase; adding a detergent, such as SDS, or sarkosyl (sodium lauroyl sarcosinate, SLS) or other anionic surfactants, e.g., sodium laureth sulfate (SLES); adding a proteinase such as proteinase K or other heat stable, broad-spectrum proteinase, such as NHSSP; adding an exonuclease, e.g., T5E; adding a DNA-staining dye; and determining the presence or absence of the inhibitor based on the fluorescence in the sample.

In one embodiment, determining the presence or absence of the inhibitor based on the fluorescence in the sample comprises comparing the fluorescence with a control, wherein a lower fluorescence in the sample than the control is indicative of the presence of the inhibitor of the DNA topoisomerase, wherein the control comprises the circular double-stranded plasmid in a supercoiled conformation. In one embodiment, the control does not comprise an inhibitor of the DNA topoisomerase. Because T5E does not digest the circular sc dsDNA, the DNA dye binds such circular sc dsDNA, leading to fluorescence higher in control than in the sample.

In certain embodiments, the control may be a positive control where a known inhibitor of the DNA topoisomerase is present. In this case, the test sample comprises an inhibitor of the DNA topoisomerase when the fluorescence in the sample is comparable to that of the control while the test sample does not comprise an inhibitor of the DNA topoisomerase when the fluorescence in the sample is higher compared to that of the control. In a specific embodiment, such positive control may comprise novobiocin and/or ciprofloxacin.

In another embodiment, both positive control and negative control are included in the method. In this case, the presence or absence of the inhibitor can be determined by the value of inhibition, which can be calculated by using equation $$\% \text{ Inhibition} = \frac{F_{NECO} - F_{TESA}}{F_{NECO} - F_{POCO}} \times 100\%,$$

where $F_{NECO}$, $F_{TESA}$, and $F_{POCO}$ are the fluorescence intensities of mixtures from the method described herein containing a negative control, the test sample, and a positive control, respectively.

In such embodiment, an inhibition of ≥30%, ≥40%, ≥50%, ≥60%, ≥70%, ≥80%, or ≥90% against an DNA gyrase may be used for indicating that the test sample comprises an inhibitor of the DNA gyrase. In a preferred embodiment, an inhibition of ≥50% against an DNA gyrase is used for indicating that the test sample comprises an inhibitor of the DNA gyrase.

In one embodiment, the method further comprises a step of removing false positive results, comprising repeating the steps of the method described herein by using the test sample in reduced concentration. The reduced concentration may be a concentration reduced by about 10%, about 20%, about 30%, about 40%, about 50%, about 60%, about 70%, about 80%, or about 90%, compared to the concentration of the test sample as initially tested in the method described herein.

In such embodiment, a positive result from repeating the steps of the method described herein by using the test sample in reduced concentrations, i.e., the test sample in reduced concentrations indicates the presence of an inhibitor of the DNA gyrase, further confirms that the test sample comprises an inhibitor of the DNA gyrase, while a negative result from repeating the steps of the method described herein by using the test sample in reduced concentrations, i.e., the test sample in reduced concentrations indicates the absence of an inhibitor of the DNA gyrase, may reverse the initial false positive result and indicate that the test sample does not comprise an inhibitor of the DNA gyrase.

In one embodiment, the subject invention provides a method for determining whether a compound is an inhibitor targeting a DNA topoisomerase, the method comprising mixing the compound with a circular double-stranded plasmid and the DNA topoisomerase; adding a detergent (e.g., SLES, SDS and/or sarkosyl) and a proteinase (e.g., proteinase K or other heat stable, broad-spectrum proteinase, such as NHSSP) to the mixture, adding an exonuclease, such as a T5E, to the mixture; adding a DNA-staining dye; and determining whether the compound is an inhibitor targeting the DNA topoisomerase based on fluorescence of the mixture.

In one embodiment, the subject invention provides a method for determining whether a compound is an inhibitor targeting DNA gyrase, the method comprising providing the compound; mixing the compound with a circular double-stranded plasmid that has the ability to interconvert between a rx configuration and a sc configuration upon supercoiling of the circular double-stranded plasmid and DNA gyrase; adding a detergent, such as SLES, SDS or sarkosyl (sodium lauroyl sarcosinate, SLS) to the mixture; adding a proteinase such as proteinase K or other heat stable, broad-spectrum proteinase, such as NHSSP to the mixture; adding T5E to the mixture; adding a DNA-staining dye; and determining whether the compound is the inhibitor targeting DNA gyrase based on the fluorescence of the mixture, wherein high fluorescence indicates that the compound is not an inhibitor of DNA gyrase while low fluorescence indicates that the compound is the inhibitor of DNA gyrase.

In one embodiment, determining whether the compound is an inhibitor based on the fluorescence of the mixture comprises comparing the fluorescence with a control, wherein a lower fluorescence in the mixture than the control indicates that the compound is an inhibitor of the DNA topoisomerase, wherein a higher or comparable fluorescence in the mixture than the control indicates that the compound is not an inhibitor of the DNA topoisomerase, wherein the control comprises the circular double-stranded plasmid in a supercoiled conformation.

In certain embodiments, the control may be a positive control where a known inhibitor of the DNA topoisomerase is present. In this case, the test compound is an inhibitor of the DNA topoisomerase when the fluorescence in the mixture is comparable to that of the control while the test compound is not an inhibitor of the DNA topoisomerase when the fluorescence in the mixture is higher compared to that of the control. In a specific embodiment, such positive control may comprise novobiocin and/or ciprofloxacin.

In another embodiment, both positive control and negative control are included in the method. In this case, whether or not the compound is an inhibitor of the DNA topoisomerase can be determined by the value of inhibition, which is calculated by using equation $$\% \text{ Inhibition} = \frac{F_{NECO} - F_{TECP}}{F_{NECO} - F_{POCO}} \times 100\%,$$

where $F_{NECO}$, $F_{TECP}$, and $F_{POCO}$ are the fluorescence intensities of mixtures from the method described herein containing a negative control, the test compound, and a positive control, respectively.

In such embodiment, an inhibition of ≥30%, ≥40%, ≥50%, ≥60%, ≥70%, ≥80%, or ≥90% against an DNA topoisomerase may be used for indicating that the test compound is an inhibitor of the DNA topoisomerase. In a preferred embodiment, an inhibition of ≥50% against an DNA topoisomerase is used for indicating that the test compound is an inhibitor of the DNA topoisomerase.

In one embodiment, the method further comprises a step of removing false positive results, comprising repeating the steps of the method described herein by using the test compound in reduced concentration. The reduced concentration may be a concentration reduced by about 10%, about 20%, about 30%, about 40%, about 50%, about 60%, about 70%, about 80%, or about 90%, compared to the concentration of the test compound as initially tested in the method described herein.

In such embodiment, a positive result from repeating the steps of the method described herein by using the test compound in reduced concentrations, i.e., the test compound in reduced concentrations indicates its identification as an inhibitor of the DNA topoisomerase, may further confirm that the test compound is an inhibitor of the DNA topoisomerase, while a negative result from repeating the steps of the method described herein by using the test compound in reduced concentrations, i.e., the test compound in reduced concentrations indicates its identification as an inhibitor of the DNA topoisomerase, may reverse the initial false positive result and indicate that the test compound is not an inhibitor of the DNA topoisomerase.

In one embodiment, the subject invention provides a method for identifying inhibitors targeting human DNA topoisomerase II, the method comprising: providing in a sample suspected of containing an inhibitor of human DNA topoisomerase II; adding a circular double-stranded plasmid; adding the DNA topoisomerase I; adding a detergent, such as SLES, SDS or sarkosyl (sodium lauroyl sarcosinate, SLS); adding a proteinase such as proteinase K or other heat stable, broad-spectrum proteinase, such as NHSSP; adding T5E; adding a DNA-staining dye; and determining the presence or absence of the inhibitor based on the fluorescence in the sample.

In certain embodiments, the method further comprises quantifying the amount of inhibitor present in the sample based on the fluorescence measured in the sample compared to the fluorescence measured in a control sample containing DNA topoisomerases such as DNA gyrase, and the circular double-stranded plasmid.

In one embodiment, the sample is suspected of containing an inhibitor of a DNA topoisomerase e.g., human DNA topoisomerase II or DNA gyrase. In a specific embodiment, the sample suspected of containing an inhibitor of a DNA topoisomerase comprises a library of compounds that potentially target DNA topoisomerases.

In certain embodiments, the T5E is added in the sample at an amount that can completely digest the fragment DNA molecule of the subject invention. For example, T5E is added in the sample at a final concentration of 10 nM to 1 mM, 10 nM to 0.5 mM, 10 nM to 0.2 mM, 10 nM to 0.1 mM, 20 nM to 0.1 mM, 50 nM to 0.1 mM, 100 nM to 0.1 mM, 150 nM to 50 µM, 100 nM to 50 µM, 100 nM to 20 µM, 100 nM to 10 µM, 100 nM to 5 µM, 150 nM to 10 µM, 150 nM to 5 µM, 150 nM to 2 µM, 150 nM to 1 µM, 150 nM to 750 nM, or 150 nM to 500 nM.

In one embodiment, the DNA dyes that can be used in the subject invention include, but are not limited to, Hoechst 33258, SYBR™ gold, ethidium bromide, EthD-1, and SYBR™ green. Preferably, the dye is SYBR™ green.

In one embodiment, the method further comprises a step of incubating the T5E in the sample prior to adding the DNA-staining dye and determining/quantifying the fluorescence of the sample. In some embodiments, the T5E is incubated with the sample for at least 5 minutes, 10 minutes, 15 minutes, 20 minutes, 25 minutes, 30 minutes, 45 minutes, 60 minutes, 90 minutes, or 120 minutes. In certain embodiments, the T5E is incubated with the sample for about 5 minutes to 5 hours, about 15 minutes to 4 hours, about 30 minutes to 3 hours, about 45 minutes to 2.5 hours, or about 1 to 2 hours.

In one embodiment, the method of the subject invention also comprises adding a nucleoside triphosphate in the sample. In a specific embodiment, the nucleoside triphosphate is ATP. In specific embodiments, the nucleoside triphosphate may be added at a maximal concentration of 12 mM, 10 mM, 9 mM, 8 mM, 7 mM, 6 mM, or 5 mM. In some embodiments, the nucleoside triphosphate may be added at a concentration of 0.01 mM to 10 mM, 0.1 mM to 10 mM, 0.5 mM to 10 mM, 1 mM to 10 mM, 2 mM to 10 mM, 3 mM to 10 mM, 4 mM to 10 mM, 5 mM to 10 mM, 1 mM to 5 mM, or 2 mM to 5 mM.

In certain embodiments, the DNA topoisomerases include, but are not limited to, type II DNA topoisomerases: type IIA and type IIB DNA topoisomerases, and type IV DNA topoisomerases. The following are some examples of DNA topoisomerases: bacterial topoisomerases, including bacterial DNA gyrase, e.g., E. coli DNA gyrase or Mtb DNA gyrase; topoisomerase IV: bacterial DNA topoisomerase IV; human topoisomerases I and IIα and other topoisomerase IA and IB topoisomerases, and other topoisomerase IIA and IIB topoisomerases. The methods can also be used to screen for yeast topoisomerase II, mammalian topoisomerase II e.g., IIa and IIb, and bacterial topoisomerase IV. In a specific embodiment, the DNA topoisomerase is selected from bacterial DNA gyrase, human DNA topoisomerase II, and bacterial topoisomerase IV.

In certain embodiments, the subject invention provides a method for determining the potency of an inhibitor of DNA topoisomerases including DNA gyrase, by evaluating the IC50 of the inhibitor. The method may comprise adding a series of concentrations of the inhibitor in the sample comprising DNA topoisomerases with the circular double-stranded plasmid of the subject invention; adding a detergent and a proteinase; adding T5E; adding a DNA-staining dye; quantifying the fluorescence of the sample; and determining the IC50 of the inhibitor.

In one embodiment, the method of the subject invention can also be used to screen potential compounds as antibacterial and/or anticancer drugs. In certain embodiments, the compounds that target DNA topoisomerases, such as DNA gyrases, may have activity against bacterial infections.

The subject invention provides assays and methods that can be used for rapid and efficient HTS, for example, in a 96-well, 384-well or 1536-well plates setting, to identify potential inhibitors from various compound libraries. Advantageously, only a small amount, e.g., a few nanograms, of the nucleic acid molecules and T5E are needed for each reaction. High-throughput screening methods can leverage robotics and automation to quickly test the biological or biochemical activity of a large number of molecules, e.g., drugs. Large scale compound libraries can quickly be screened in a cost-effective way to accelerate target analysis and assess pharmacologically profiling agonists and antagonists for receptors and enzymes.

In some embodiments, the subject invention provides methods for HTS to identify inhibitors of one or more enzymes that affects the DNA topology, the method comprising providing a sample carrier, e.g., HTS plates such as microplate, comprising arrays of individual reservoir, each reservoir containing a compound of a screening library or a control, adding a circular dsDNA molecule of the subject invention and an enzyme in each reservoir; adding a detergent and a proteinase; adding an exonuclease, e.g., T5E, in each reservoir; adding a DNA-staining dye; determining the inhibitors of one or more enzymes based on the fluorescence in each reservoir.

In a specific embodiment, the HTS assay uses 150 nM of E. coli DNA gyrase, 50 µM of ciprofloxacin (for positive controls), 200 nM of T5 exonuclease, 100' dilution of DNA samples, and 1' SYBR™ Green.

In a specific embodiment, the DNA gyrase inhibitors are, for example, quinolones including levofloxacin, ciprofloxacin, oxolinic acid, enrofloxacin, norfloxacin, lomefloxacin, and nalidixic acid.

In one embodiment, the subject invention provides a method for producing linear and nicked plasmid DNA molecules for the assays and method of the subject invention.

In one embodiment, the subject invention also provides kits for screening inhibitors of DNA topoisomerases, e.g., human topoisomerase II and DNA gyrase. The kit can comprise, for example, a circular double-stranded DNA plasmid of the subject invention, a DNA topoisomerase, a detergent such as SLES, SDS or sarkosyl, a proteinase such as proteinase K or other heat stable, broad-spectrum proteinase, such as NHSSP, a DNA-staining dye and T5E.

The kits may further be used in the methods described herein. The kits may also include at least one reagent and/or instructions for their use. Also, the kits may include one or more containers filled with reagent(s), and/or one or more molecules for use according to the invention. The kits may also comprise a control composition, nucleoside triphosphates and/or buffers. In a specific embodiment, the control composition may comprise novobiocin and/or ciprofloxacin.

In certain embodiments, the kits may additionally include reagents and means for detecting the labels provided on the molecules used according to the invention. As it would be understood by those skilled in the art, additional detection or labeling methodologies may be used in the kits provided.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Materials and Methods

Proteins, Plasmids, and Other Reagents

E. coli DNA gyrase, T5 exonuclease, and His-tagged human DNA topoisomerase IIα C-terminal deletion mutant (hTopo2α-ΔCTD) were purified. Plasmid pBR322 and lambda DNA HindIII digest were purchased from New England Biolabs, Inc (Ipswich, MA). Relaxed pBR322 was prepared using variola DNA topoisomerase I purified in the lab. Ciprofloxacin, etoposide, sodium dodecyl sulfate (SDS), and sarkosyl or sodium lauroyl sarcosinate (SLS) were purchased from Sigma-Aldrich, Inc. SYBR™ Green I was bought from ThermoFisher Scientific, Inc. NSC compounds were obtained from NCI DTP program (dtp.cancer.gov).

DNA Gyrase and Human DNA Topoisomerase IIα Mediated DNA Cleavage Assay.

250 ng of relaxed plasmid pBR322 and 20 nM of E. coli DNA gyrase or human DNA topoisomerase IIα were mixed and incubated in 1×gyrase-mediated DNA cleavage buffer (20 mM Tris-HCl pH 8, 50 mM KAc, 10 mM $MgCl_2$, 2 mM DTT, 1 mM ATP, 0.1 mg/mL BSA) at 37° C. for 15 minutes in the presence of an inhibitor or compound. After the incubation, 0.2% SDS and 0.1 mg/ml proteinase K were added to the reaction mixtures to trap the topoisomerase-inhibitor-DNA complex and digest the topoisomerase, respectively, by incubating for an additional 30 min at 37° C. DNA samples were analyzed in 1% agarose gel containing 0.5 g/mL ethidium bromide in 1'TAE buffer and photographed under UV light. Ciprofloxacin was used as a positive control for E. coli DNA gyrase-mediated DNA cleavage assays. Etoposide was used as a positive control for human DNA topoisomerase IIα-mediated DNA cleavage assays.

A Fluorescence-Based, T5 Exonuclease-Amplified DNA Cleavage Assay to Identify Poisoning Inhibitors for E. coli DNA Gyrase.

The fluorescence-based, gyrase-mediated DNA cleavage assays were performed in 20 μL of 1× gyrase-mediated DNA cleavage buffer (20 mM Tris-HCl pH 8, 50 mM KAc, 10 mM $MgCl_2$, 2 mM DTT, 1 mM ATP, 0.1 mg/mL BSA) containing 200 ng of Rx pBR322 and 0.05 mg/mL (136.5 nM) of E. coli DNA gyrase in the absence or presence of a potential gyrase poisoning inhibitor. For positive control experiments, 50 μM of ciprofloxacin was used. For negative control experiments, 1% DMSO was used. After 60 min of incubation at 37° C., 0.125% of sarkasyl (final concentration) was added to trap the drug-gyrase-DNA complexes. 0.5 mg/mL of proteinase K was then added to the reaction mixtures to digest DNA gyrase at 50° C. for 30 min. After the DNA samples were diluted 100 times using 1×NEB buffer 4 (20 mM Tris-Acetate, pH 7.9, 50 mM KAc, 10 mM $Mg(AC)_2$, and 1 mM DTT), 30 μL of each DNA sample was transfer to a well of a 384-well plate. 200 nM of T5 exonuclease was used to digest DNA fragment for 2 hours at 37° C. 1×SYBR™ Green was added to all DNA samples. Fluorescence intensity was measured using a Biotek microplate reader with excitation wavelength of 497 nm and emission wavelength of 525 nm.

Z-factor (Z') was determined using 96 wells of a 384-well plate where 48 wells are for positive controls in the presence of 50 µM of ciprofloxacin and the rest 48 wells for negative controls in the absence of ciprofloxacin. Z' was calculated by the following equation:

$$Z' = 1 - \frac{3(\sigma_p + \sigma_n)}{|\mu_p - \mu_n|}$$

where $\sigma_p$, $\sigma_n$, $\mu_p$ and $\mu_n$ represent the sample means and standard deviations for positive (p) and negative (n) controls, respectively.

Example—1 the Fluorescence-Based, T5 Exonuclease-Amplified DNA Cleavage Assay

Figure 1B:
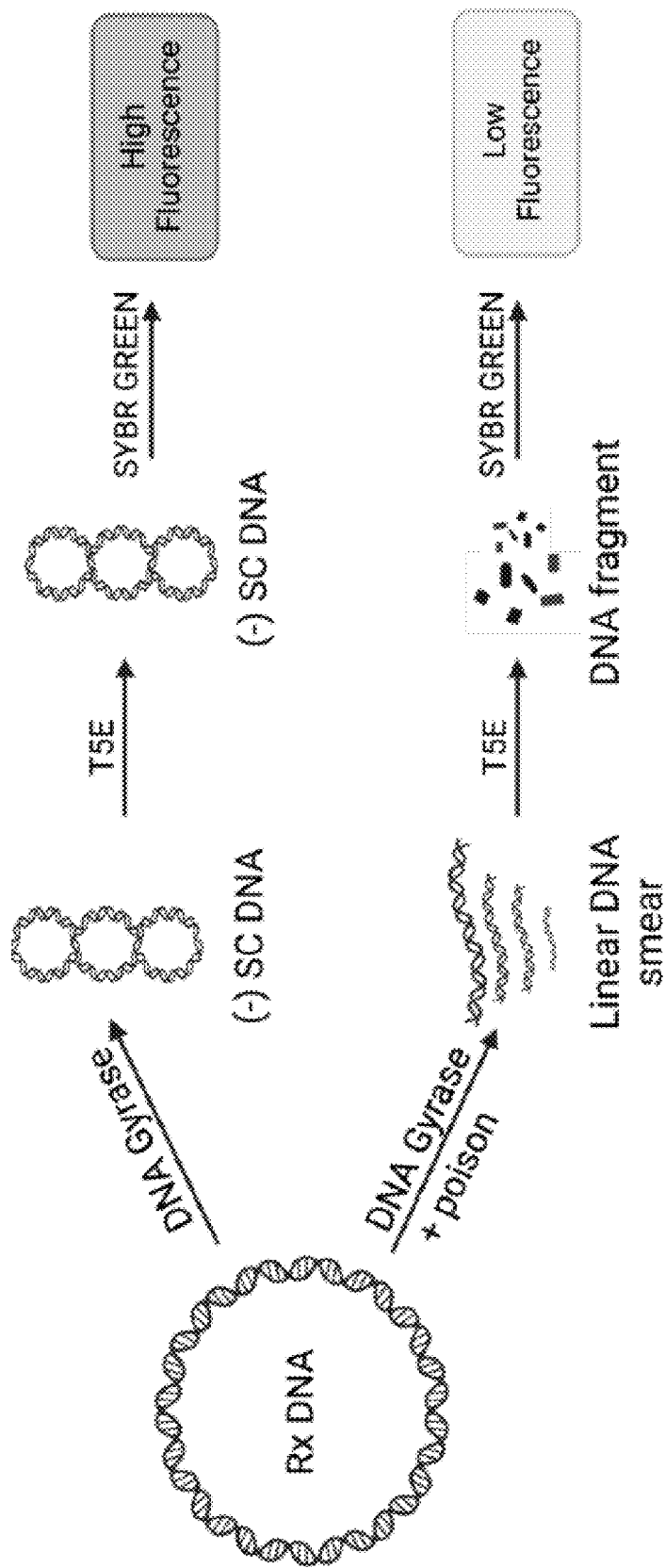

FIG. 1 shows the principle and experimental strategy for a fluorescence-based, T5 exonuclease-amplified DNA cleavage assay to discover bacterial DNA gyrase poisoning inhibitors. It shows that multiple DNA gyrase molecules simultaneously bind to a plasmid DNA molecule to form a gyrase-plasmid complex, which leads to the formation of multiple gyrase-DNA cleavage complexes on the same plasmid DNA molecule (FIG. 1A). In the presence of a DNA gyrase poisoning inhibitor, such as ciprofloxacin, these gyrase-DNA cleavage complexes can be trapped by SDS or sarkosyl (sodium lauroyl sarcosinate, SLS). After proteinase K digestion of gyrase, fragmented linear DNA molecules are produced. T5 exonuclease, which selectively digests linear and nicked DNA while leaving supercoiled and relaxed plasmid DNA intact, can be used to completely digest the fragmented linear DNA molecules and "amplify" the difference of the remaining DNA molecules in the DNA cleavages assays between the presence and absence of a poisoning gyrase inhibitor (FIG. 1B). The decrease in the plasmid can be detected using SYBR™ green staining dye or quantitative polymerase chain reaction (qPCR). Since this is a fluorescence-based assay, it can be configured into a miniaturized, automated system (e.g., HTS assay) capable of identifying DNA gyrase poisoning inhibitors through the screening of compound libraries containing thousands or millions of compounds. Importantly, this assay is not only capable of detecting gyrase poisons that result in double-stranded DNA breaks but also identify gyrase poisons that lead to single-stranded DNA breaks, such as NTBIs (e.g., gepotidacin).

Figure 2A:
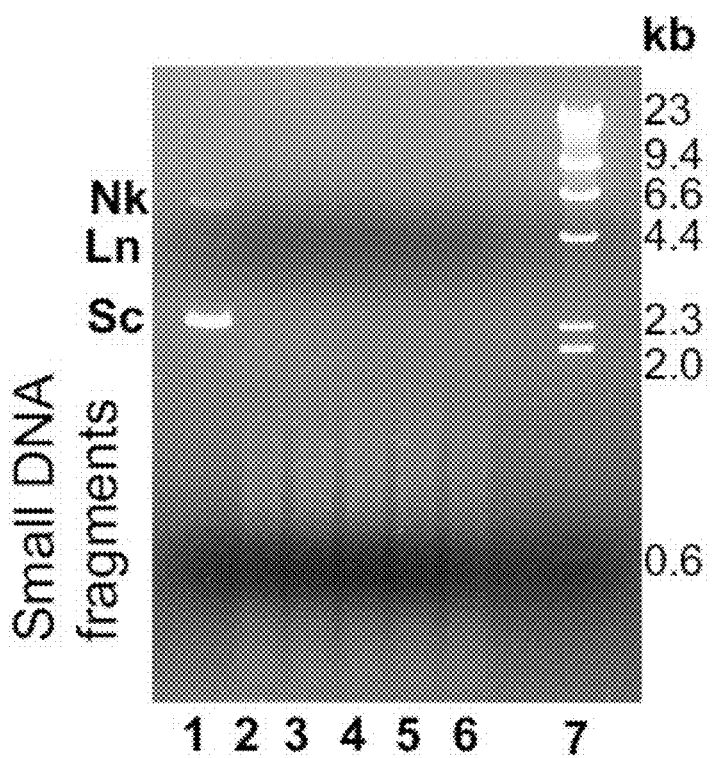
FIGS. 2A-2F. Agarose gel-based DNA gyrase cleavage assays were performed as described in Materials and Methods. (A) Very high concentrations of E. coli DNA gyrase (150 nM) cleaved plasmid pBR322 into small DNA fragments in the presence of 50 µM of ciprofloxacin in the gyrase-mediated DNA cleavage assays. Lane 1 is the DNA sample from the reaction mixture in the absence of ciprofloxacin. Lanes 2-6 contain DNA samples from the reaction mixtures containing 50 µM of ciprofloxacin. Lane 7 is Lambda DNA HindIII digest as the molecular standard. (B) Sufficient amount of ciprofloxacin is required for the cleavage of plasmid pBR322 into small DNA fragments. Lanes 1-8 contain 0, 0.5, 1, 2, 5, 10, 25, 50 µM of ciprofloxacin, respectively. (C) The appearance and disappearance of the gyrase-mediated linear band of plasmid pBR322 is dependent of the E. coli DNA gyrase concentration. High concentrations of E. coli DNA gyrase also cause disappearance of the supercoiled plasmid in the gyrase-mediated DNA cleavage assays. (D) SDS potently inhibited T5 exonuclease (T5E) activity. 500 ng of a DNA HindIII digest was digested using 50 nM of T5E in 20 µL of 1× gyrase-mediated DNA cleavage buffer (20 mM Tris-HCl pH 8, 50 mM KAc, 10 mM MgCl2, 2 mM DTT, 1 mM ATP, 0.1 mg/mL BSA) for 30 min in the presence of different concentrations of SDS. Lanes 2-8 contained 0.000625, 0.00125, 0.0025, 0.005, 0.0125, and 0.025%, respectively. (E) Effects of sarkosyl on T5 exonuclease (T5E). 500 ng of a DNA HindIII digest was digested using 50 nM of T5E in 20 µL of 1× gyrase-mediated DNA cleavage buffer for 30 min in the presence of different concentrations of sarkosyl. Lanes 3 to 10 contained 0.005, 0.0125, 0.015, 0.02, 0.025, 0.05, 0.125, and 0.25%, respectively. (F) 50 nM of T5 exonuclease completely digested 500 ng of a DNA HindIII digest in 1× gyrase-mediated DNA cleavage buffer in the presence of 0.00125%. Lanes 1-7 contained 0, 5, 10, 20, 30, 40, and 50 nM of T5 exonuclease, respectively.
Figure 2B:
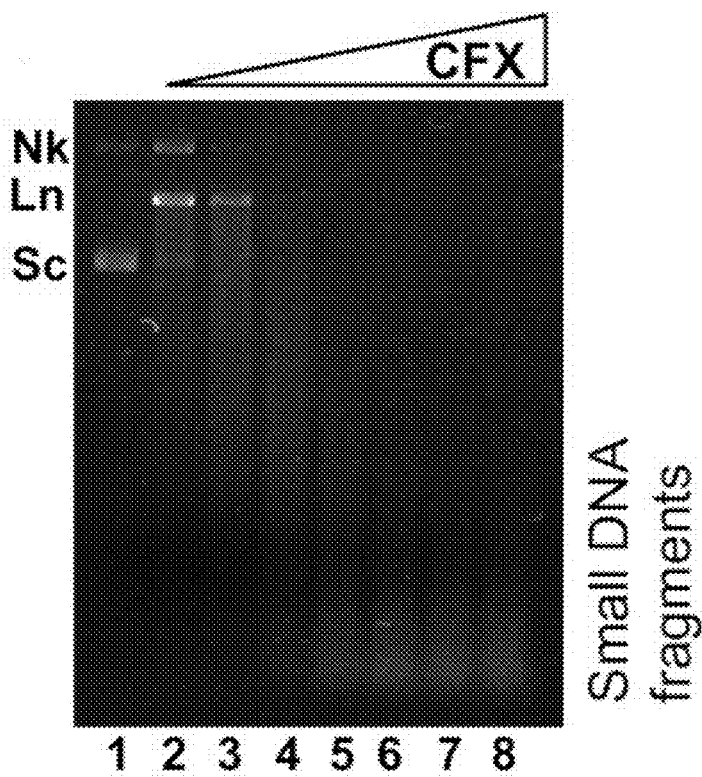

In the presence of 50 µM of ciprofloxacin and a high concentration of E. coli DNA gyrase, e.g., 150 nM of E. coli DNA gyrase, all plasmid pBR322 molecules were converted into small DNA fragments (FIG. 2A). The fragmentation of plasmid DNA pBR322 was contingent upon the presence of ciprofloxacin (compare lane 1 to lanes 2-6 of FIG. 2A) and correlated with the ciprofloxacin concentration (FIG. 2B). A DNA gyrase titration experiment was performed for the gyrase-mediated DNA cleavage assays and a progressive increase in the linear plasmid DNA products was observed when using increasing concentrations of E. coli DNA gyrase in the presence of 50 µM of ciprofloxacin (FIG. 2C).

Figure 2C:
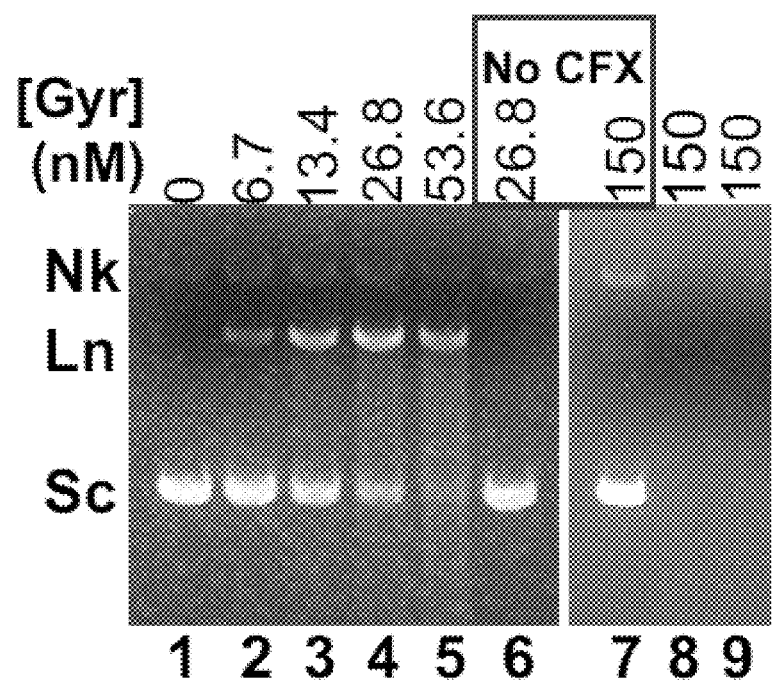

Also, DNA smears started from the linear band and went through the supercoiled band for the two assays when 26.8 and 53.6 nM of DNA gyrase were used (lanes 4 and 5 of FIG. 2C). Correspondingly, the supercoiled DNA bands were significantly reduced in these lanes. As expected and also consistent with the results in FIG. 2A, when 150 nM of DNA gyrase was present, the supercoiled plasmid DNA template disappeared completely (lanes 8 and 9 of FIG. 2C). These results strongly support that the presence of two or more gyrase molecules on a plasmid molecule caused several DNA breaks, leading to the formation of multiple gyrase-DNA cleavage complexes. These gyrase-DNA cleavage complexes, stabilized by ciprofloxacin, were subsequently entrapped by SDS or sarkosyl. After proteinase K digestion of gyrase, fragmented linear DNA molecules were produced (FIG. 1A). Furthermore, these results serve as the foundation for the fluorescence-based, T5 exonuclease-amplified DNA cleavage assay (FIG. 1B).

Figure 2D:
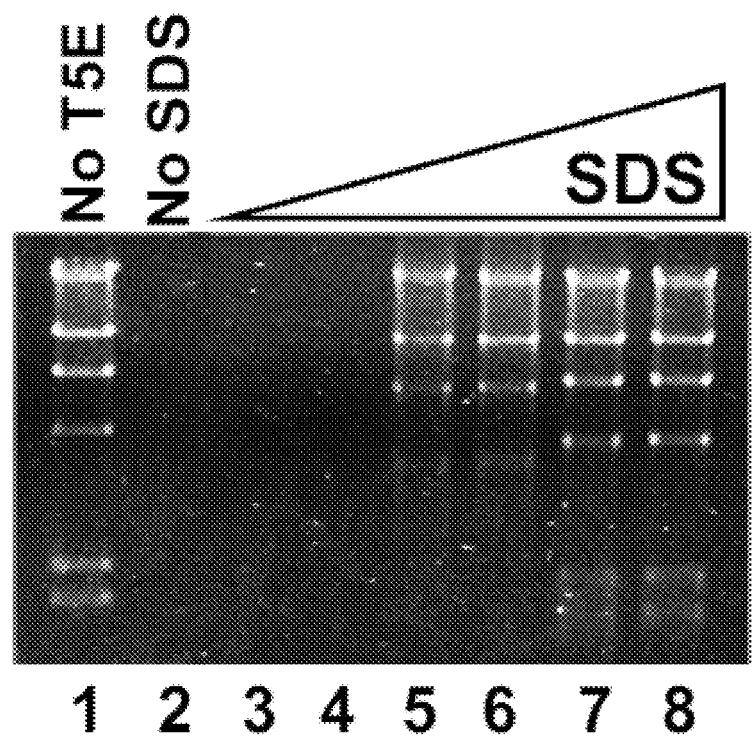
Figure 2E:
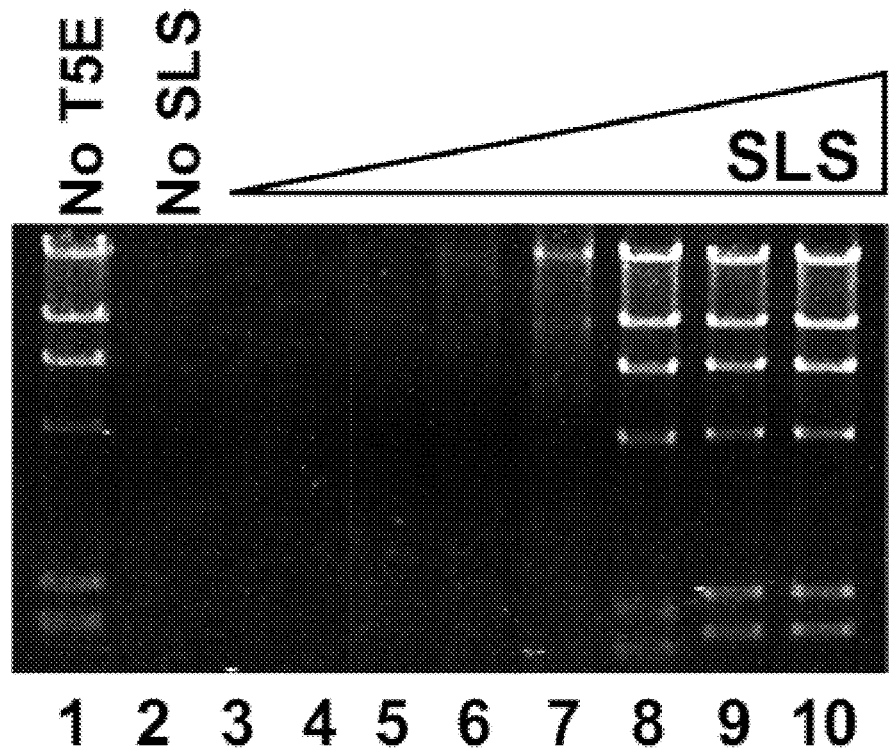
Figure 2F:
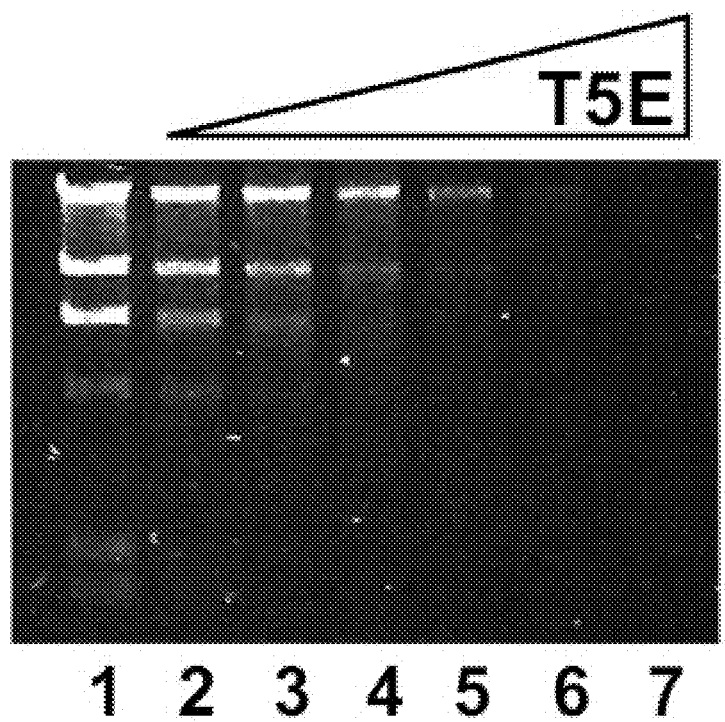

In a typical gyrase-mediated DNA cleavage assay, SDS or sarkosyl is used to trap the drug-gyrase—DNA complexes. The results showed that low concentrations of SDS completely inhibited T5 exonuclease activity (FIG. 2D). However, relatively high concentrations of sarkosyl (e.g., 0.015%) did not significantly affect T5 exonuclease's activity (FIG. 2E). Therefore, sarkosyl was used to trap the drug-gyrase-DNA complexes in the following assays. Indeed, 50 nM of T5 exonuclease completely digested 250 ng of lambda DNA HindIII digest in 30 min in the presence of sarkosyl (FIG. 2F).

Figure 3:
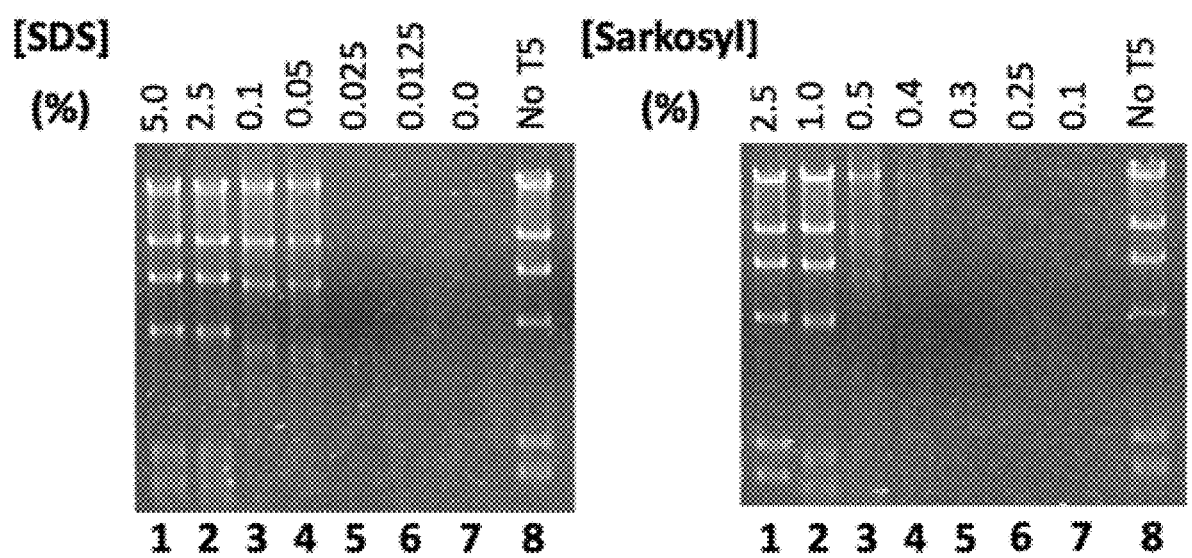
FIG. 3. Detergent inhibition of T5 Exonuclease (T5) on lambda DNA Hind III digest. Lanes 1-7 contain 4.0 µM of T5 exonuclease. Lane 8 contains no T5 exonuclease. SDS concentrations≥0.05% inhibits T5 exonuclease. Sarkosyl concentrations≥0.5% inhibits T5 exonuclease.
Figure 4B:
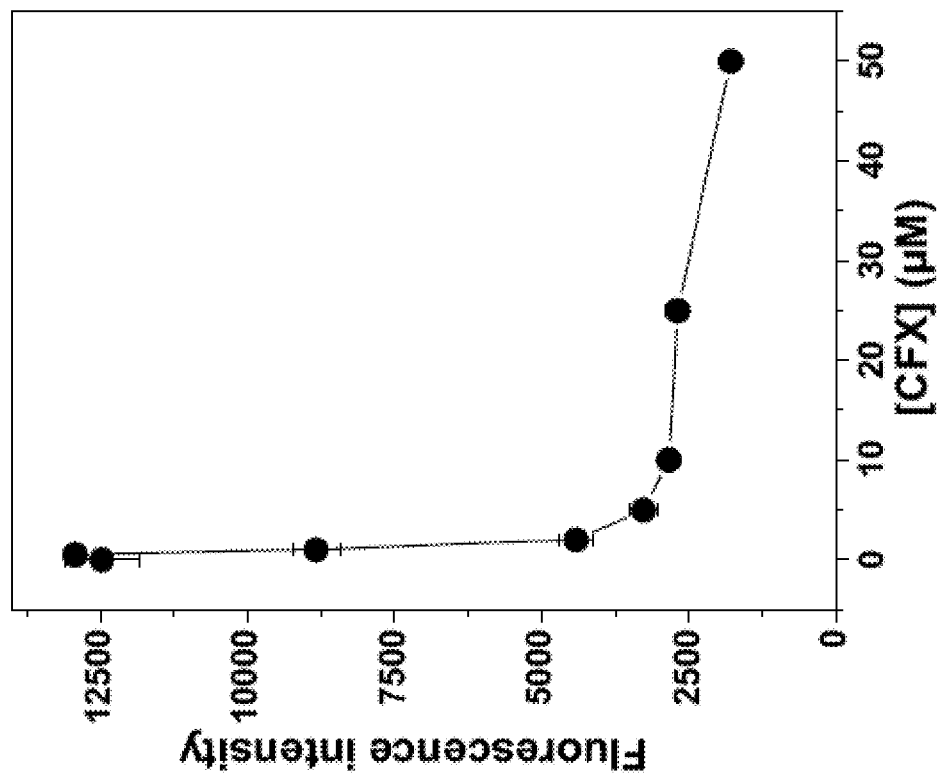
FIGS. 4A-4F. Determining the optimal conditions for the fluorescence-based, T5 exonuclease-amplified DNA cleavage assay for E. coli DNA gyrase. The fluorescence-based, T5 exonuclease-amplified DNA cleavage assay for E. coli DNA gyrase was described in Materials and Methods. The fluorescence intensity was measured with λ em=525 nm and λ ex=497 nm using a plate reader. (A-D) gray and black dots-lines represent assays in the absence and presence of ciprofloxacin (CFX). (A) *E. coli* gyrase titration experiments. (B) Ciprofloxacin titration experiment. (C) T5 exonuclease titration experiment. (D) Time courses for T5 exonuclease digestion. 200 nM of T5 exonuclease was used in each assay. (E) Dilution effect of DNA samples before T5 exonuclease digestion. (F) SYBR™ Green titration experiment.
Figure 4A:
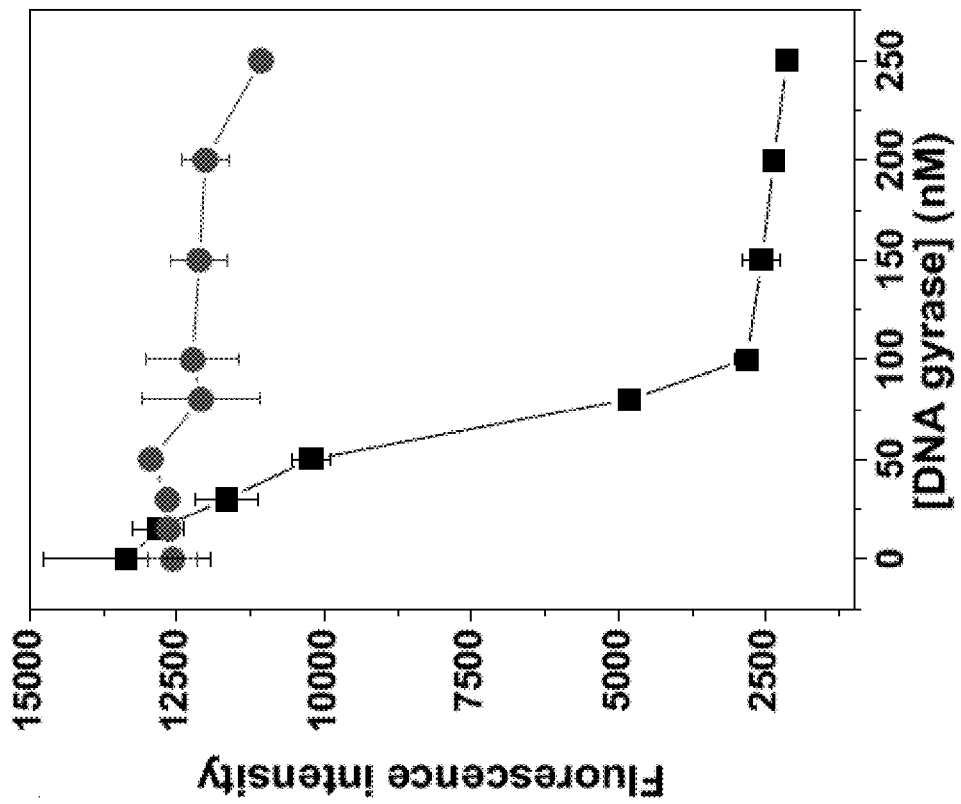
Figure 4D:
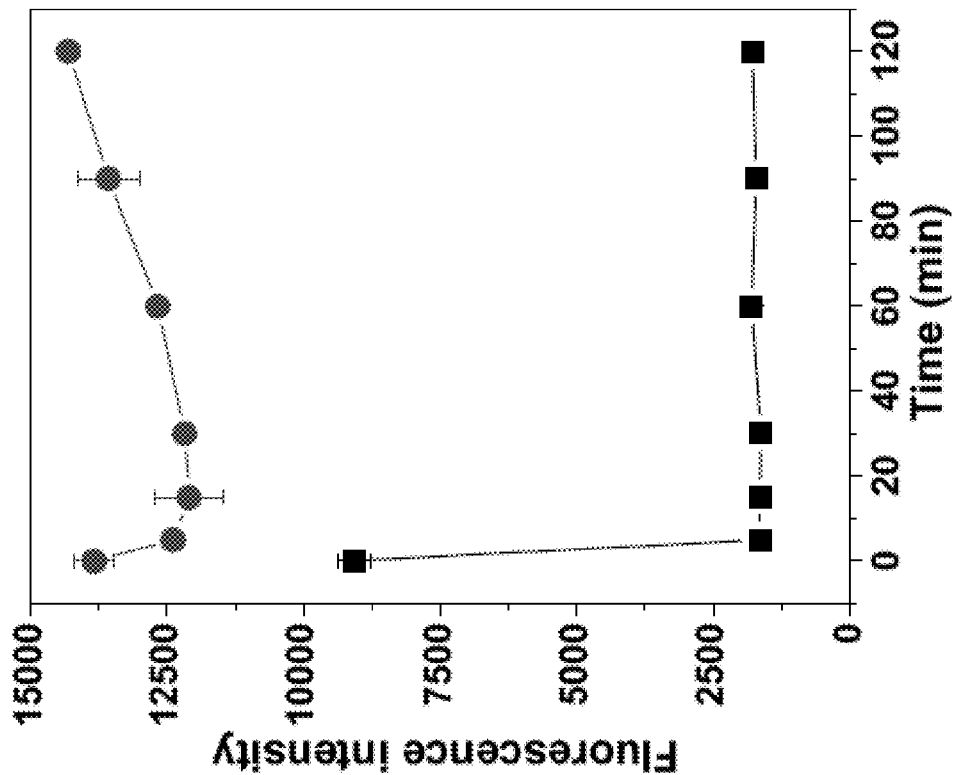
Figure 4C:
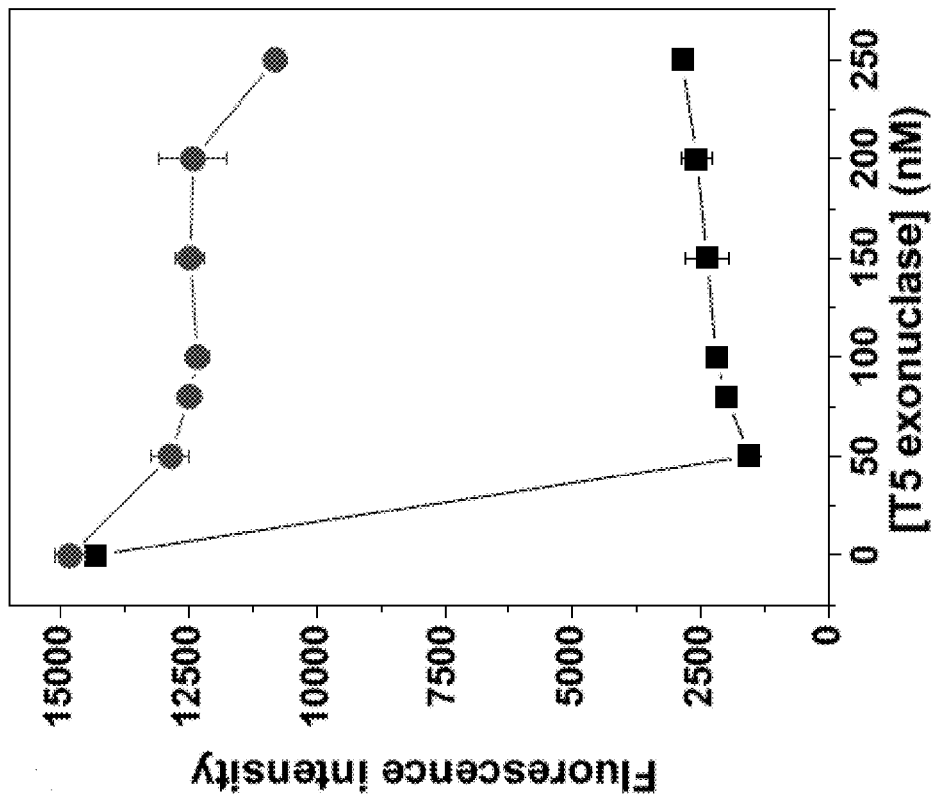
Figure 4E:
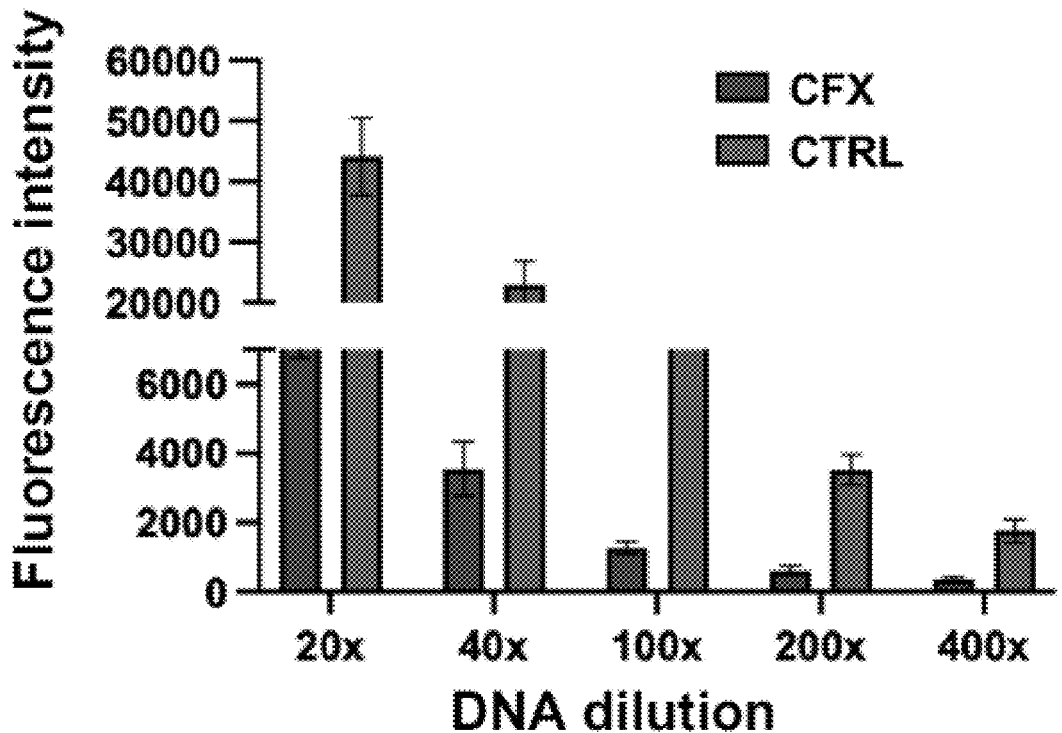
Figure 4F:
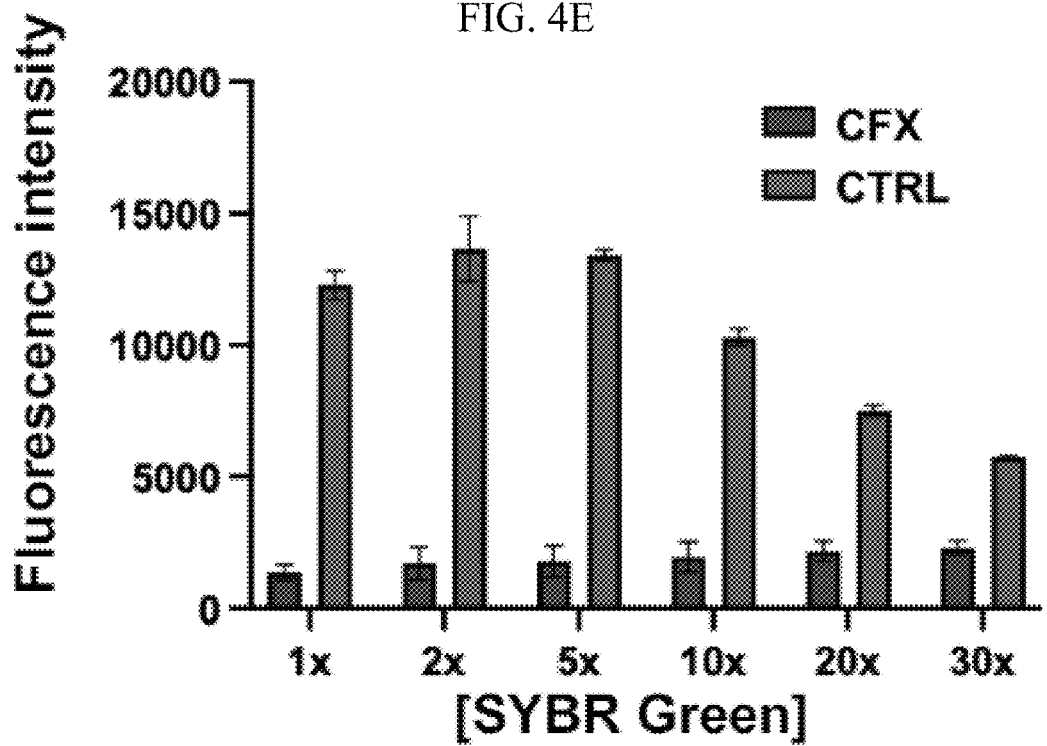

FIG. 3 also shows the detergent inhibition of T5 Exonuclease (T5) on lambda DNA Hind III digest. Lanes 1-7 contain 4.0 µM of T5 exonuclease. Lane 8 contains no T5 exonuclease. SDS concentrations≥0.05% inhibits T5 exonuclease. Sarkosyl concentrations≥0.5% inhibits T5 exonuclease.

A series of experiments were performed to determine the optimal conditions for the T5 exonuclease-amplified fluorescence-based DNA cleavage HTS assay for E. coli DNA gyrase (FIG. 4). For example, in the presence of ciprofloxacin, the fluorescence intensity of the DNA samples is progressively decreased when the concentration of E. coli DNA gyrase was increased (FIG. 4A). It reached a plateau when 100 nM of E. coli DNA gyrase was used (FIG. 4A). In contrast, the concentration of E. coli DNA gyrase did not significantly change the fluorescence intensity for the DNA samples in the absence of ciprofloxacin (FIG. 4A). The fluorescence intensity of the DNA samples also depended on the ciprofloxacin concentration (FIG. 4B). T5 exonuclease greatly "amplified" the fluorescence difference/signal of the DNA samples between the presence and absence of ciprofloxacin (FIGS. 4C and D). Dilution of the DNA samples significantly minimized the effects of sarkosyl on the digestion of DNA samples by T5 exonuclease (FIG. 4E). 1' and 2' SYBR™ Green provided the best results for the HTS assays (FIG. 4F). These experiments showed that 136.5 nM of E. coli DNA gyrase, 50 µM of ciprofloxacin (for positive controls), 200 nM of T5 exonuclease, a 100-folder dilution of DNA samples, and 1×SYBR™ Green are optimal and were chosen for the HTS assay. The assay tolerated up to 2% DMSO without any significant change in signal. The titration experiment in which different concentrations of ciprofloxacin were added into the assays showed that ciprofloxacin potently inhibited the activities of DNA gyrase and progressively cleaved DNA with an estimated EC50 values of 1.48 µM (FIG. 4B).

Example—2. Identify Bacterial DNA Gyrase Poisons

Figure 5A:
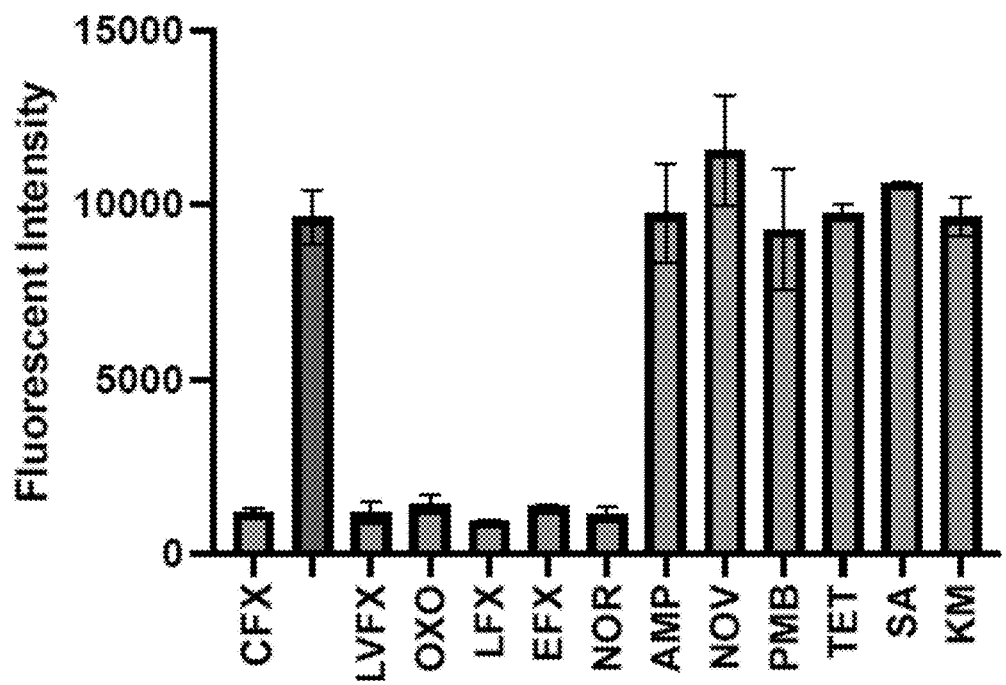
FIGS. 5A-5B. The fluorescence-based, T5 exonuclease-amplified DNA gyrase cleavage assay for 10 different antibiotics, 5 fluoroquinolones and 5 other antibiotics were performed in 20 μL of 1× gyrase-mediated DNA cleavage buffer containing 200 ng of Rx pBR322 and 0.05 mg/mL (136.5 nM) of *E. coli* DNA gyrase in the absence or presence of an antibiotics. For control experiments, 50 μM of ciprofloxacin was used. After 60 min of incubation at 37° C., 0.125% of sarkasyl was added to trap the drug-gyrase-DNA complexes. 0.5 mg/mL of proteinase K was then added to the reaction mixtures to digest DNA gyrase at 50° C. for 30 min. After the DNA samples were diluted 100 times using 1×NEB buffer 4, 200 nM of T5 exonuclease was used to digest DNA fragment for 2 hours at 37° C. 1×SYBR™ Green was added to all DNA samples. (A) Fluorescence intensity was measured using a Biotek microplate reader with excitation wavelength of 497 nm and emission wavelength of 525 nm. (B) 1% agarose gels containing 0.5 μg/mL of EB in 1×TAE for DNA samples before the 100 times of dilution. Lanes 8 and 14 did not contain a compound. Abbreviations: Nov, novobiocin; CFX, ciprofloxacin; OXO, oxolinic acid; LFX, lomefloxacin; EFX, enrofloxacin; NOR, norfloxacin; AMP, ampicillin; PMB, polymyxin B sulfate; TET, tetracycline SA, sulfanilamide; KM, kanamycin.
Figure 5B:
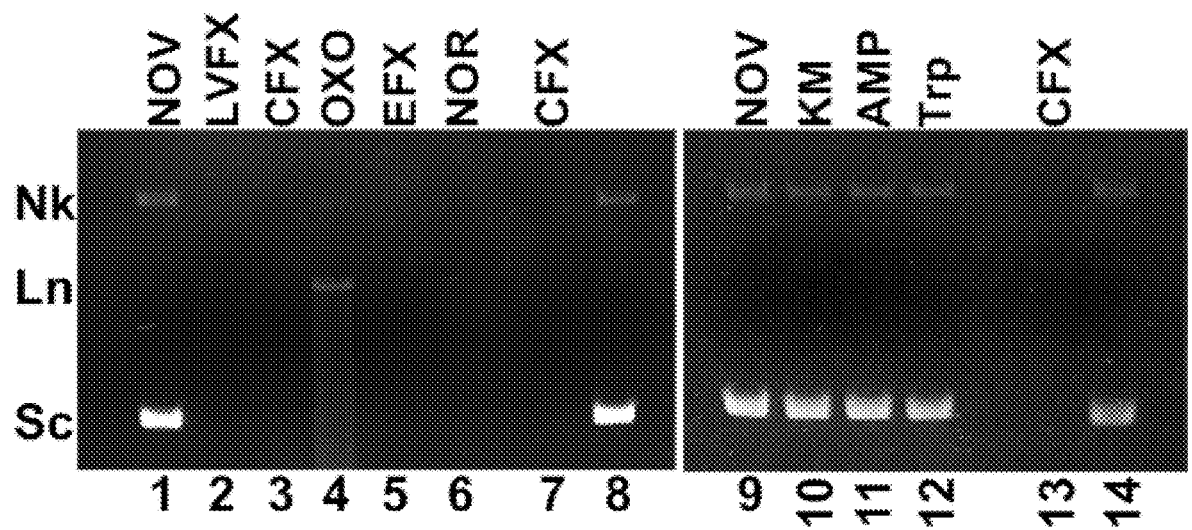

For validation, an experiment was conducted using this assay with 10 compounds-five FQs and five other antibiotics (novobiocin, ampicillin, polymyxin B, sulfanilamide, and kanamycin). The results are shown in FIGS. 5A and B. The fluorescence intensity of the DNA samples in the presence of FQs was significantly low, whereas the fluorescence intensity of the DNA samples in the presence of other antibiotics, including novobiocin, was high. Interestingly, novobiocin, a DNA gyrase catalytical inhibitor targeting the gyrase ATPase, did not cause a decrease in fluorescence intensity. These results demonstrate the feasibility of the assay, specifically designed to identify DNA gyrase poisoning inhibitors/poisons.

Figure 6A:
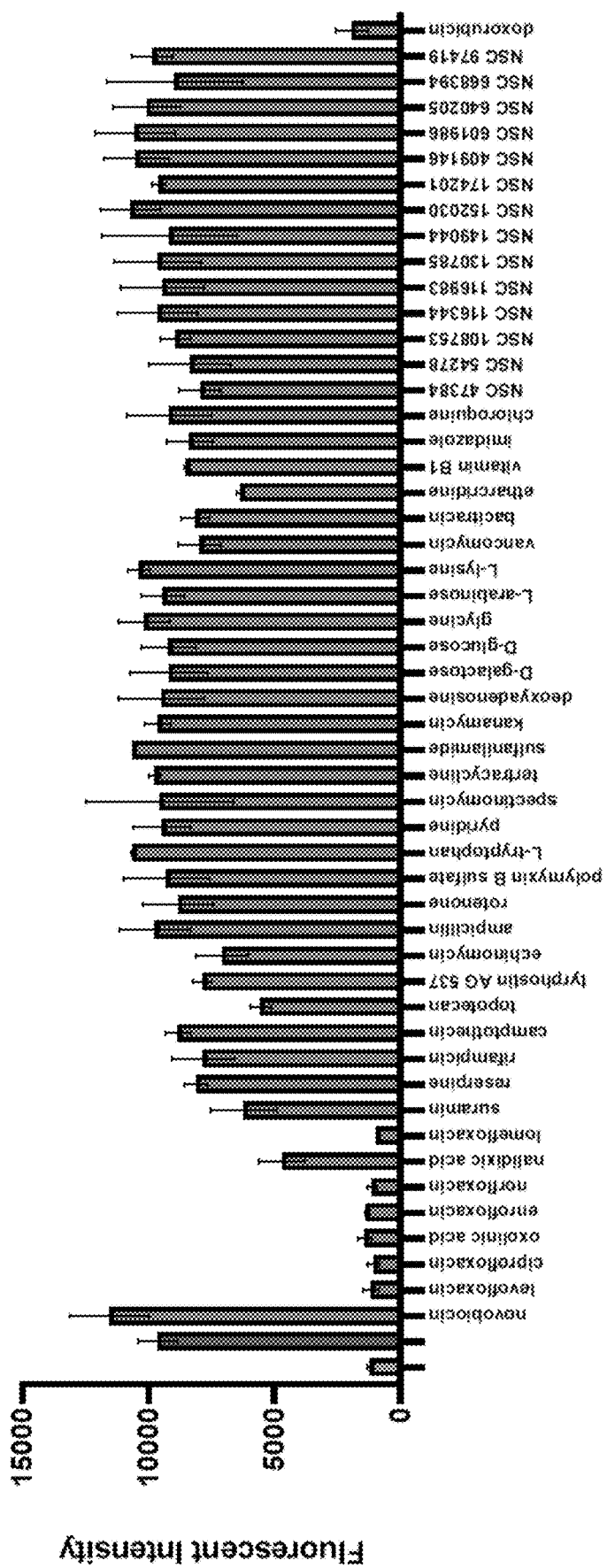
FIGS. 6A-6B. High throughput screening (HTS) pilot screen of the 50-compound library for *E. coli* DNA gyrase poisoning inhibitors in duplicate. A final compound concentration of 50 μM was used. DMSO (1%) (second bar) and ciprofloxacin (50 μM) (first bar) are used as negative and positive controls, respectively. (A) Fluorescence raw data. (B) Inhibition is calculated by using equation % Inhibition=$F_{DMSO}-F_{CPD}/F_{DMSO}-F_{CFX}\times 100\%$ where $F_{DMSO}$, $F_{CPD}$, and $F_{CFX}$ are fluorescence intensity of DNA samples from DNA cleavage assays containing 1% DMSO (as negative controls; gray), a compound (CPD), and ciprofloxacin (CFX; light gray), respectively. An inhibition of≥50% against *E. coli* DNA gyrase is used as the cutoff value for gyrase poisoning inhibitors, which results in 8 hits.
Figure 6B:
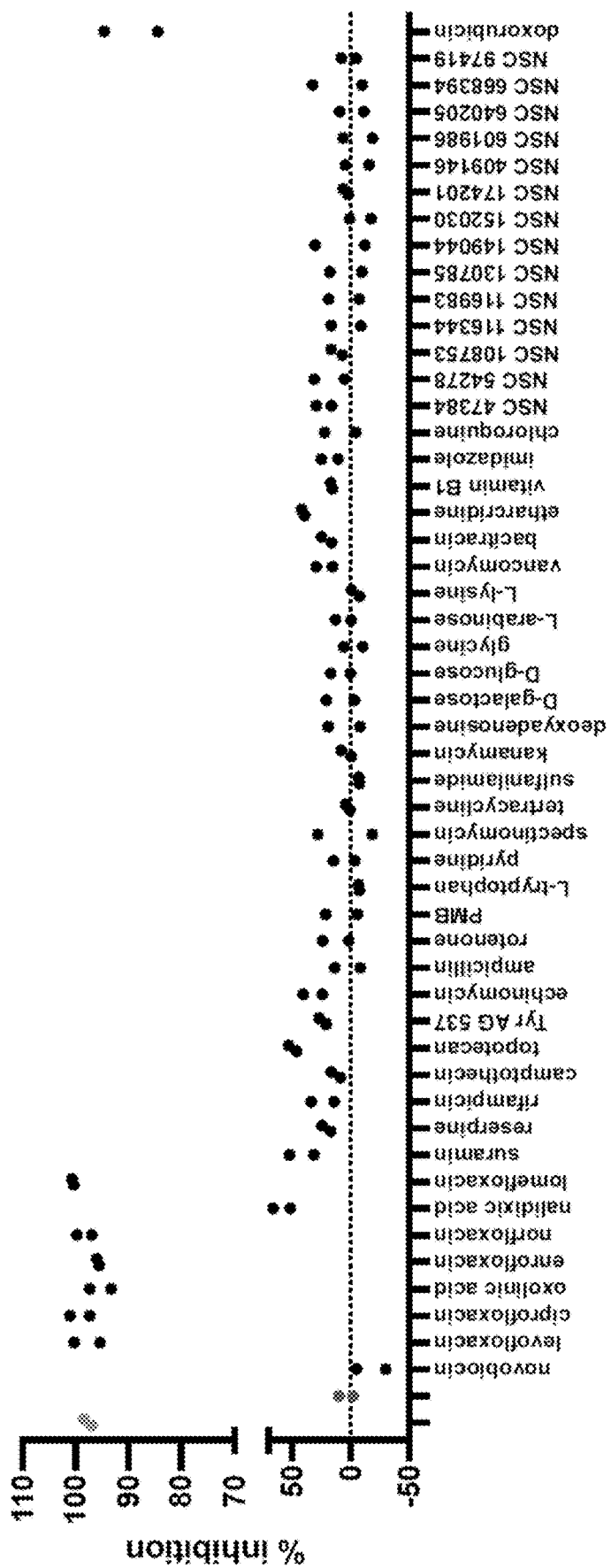

Next, a 50-compound library was screened using this assay at a final compound concentration of 50 μM in duplicate and got the following statistics: Z', 0.53; S/B, 7.3; and 8 hits (FIG. 6 and Tables 1 and 2).

TABLE 1

Parameters for the fluorescence-based, T5 exonuclease-amplified HTS assay for *E. coli* DNA gyrase using the 50-compound library.

| # of compounds | 50 |
| Tested concentration | 50 μM |
| Z' value | 0.53 |
| [a]S/B | 7.3 |
| # of compounds with inhibition >50% | 8 |

[a]S/B represents signal versus background ratio

TABLE 2

Raw data for 50 compound library screening

| Compound | Fluorescent Intensity #1 | Fluorescent Intensity #2 | Mean Fluorescent Intensity | Standard deviation | CID |
| --- | --- | --- | --- | --- | --- |
| novobiocin | 10440 | 14678 | 12559 | 2996.718539 | 54675769 |
| levofloxacin | 1417 | 974 | 1195.5 | 313.2483041 | 149096 |
| ciprofloxacin | 1236 | 910 | 1073 | 230.5168107 | 2764 |
| oxolinic acid | 1607 | 1239 | 1423 | 260.2152955 | 4628 |
| enrofloxacin | 1402 | 1360 | 1381 | 29.69848481 | 71188 |
| norfloxacin | 1276 | 1020 | 1148 | 181.019336 | 4539 |
| nalidixic acid | 4041 | 5349 | 4695 | 924.8956698 | 4421 |
| lomefloxacin | 967 | 940 | 953.5 | 19.09188309 | 3948 |
| suramin | 5287 | 7152 | 6219.5 | 1318.754147 | 5361 |
| reserpine | 8439 | 7797 | 8118 | 453.9625535 | 5770 |
| rifampicin | 8717 | 6951 | 7834 | 1248.750576 | 135398735 |
| camptothecin | 9196 | 8486 | 8841 | 502.0458146 | 24360 |
| topotecan | 5838 | 5232 | 5535 | 428.5067094 | 60700 |
| tyrphostin AG 537 | 8123 | 7583 | 7853 | 381.8376618 | 5329255 |
| echinomycin | 8332 | 9828 | 9080 | 1057.831745 | 3197 |
| ampicillin | 10742 | 8755 | 9748.5 | 1405.021174 | 6249 |
| rotenone | 7837 | 9818 | 8827.5 | 1400.778534 | 6758 |
| polymyxin B sulfate salt | 6067 | 10508 | 8287.5 | 3140.261215 | 4868 |
| L-tryptophan | 12595 | 10673 | 11634 | 1359.059233 | 6305 |
| pyridine | 8664 | 10294 | 9479 | 1152.584053 | 1049 |
| spectinomycin | 7472 | 11649 | 9560.5 | 2953.585025 | 15541 |
| tertracycline | 9594 | 9920 | 9757 | 230.5168107 | 54675776 |
| sulfanilamide | 10634 | 10620 | 10627 | 9.899494937 | 5333 |
| kanamycin | 9267 | 10024 | 9645.5 | 535.2798334 | 6032 |
| deoxyadenosine | 4274 | 6701 | 5487.5 | 1716.148158 | 13730 |
| D-galactose | 4111 | 6277 | 5194 | 1531.593288 | 6036 |
| D-glucose | 4444 | 5984 | 5214 | 1088.944443 | 5793 |
| glycine | 5450 | 6905 | 6177.5 | 1028.840367 | 750 |
| L-arabinose | 4824 | 7032 | 5928 | 1561.291773 | 439195 |
| L-lysine | 5067 | 6689 | 5878 | 1146.927199 | 5962 |
| vancomycin | 7361 | 6582 | 6971.5 | 550.8361825 | 14969 |
| bacitracin | 7743 | 6533 | 7138 | 855.5992052 | 11980094 |
| etharcridine | 7470 | 6233 | 6851.5 | 874.6910883 | 2017 |
| vitamin B1 | 8458 | 6561 | 7509.5 | 1341.381564 | 135418510 |
| imidazole | 9023 | 7731 | 8377 | 913.5819613 | 795 |
| chloroquine | 10376 | 8002 | 9189 | 1678.671499 | 2719 |
| NSC 47384 | 8526 | 7341 | 7933.5 | 837.9215357 | 240739 |
| NSC 54278 | 9502 | 7208 | 8355 | 1622.102956 | 243964 |
| NSC 108753 | 9358 | 8489 | 8923.5 | 614.4757929 | 268501 |
| NSC 116344 | 10770 | 8502 | 9636 | 1603.71818 | 113169 |
| NSC 116983 | 8282 | 10627 | 9454.5 | 1658.165402 | 272529 |
| NSC 130785 | 8402 | 10853 | 9627.5 | 1733.118721 | 279596 |
| NSC 149044 | 7269 | 11063 | 9166 | 2682.763128 | 288280 |
| NSC 152030 | 9897 | 11565 | 10731 | 1179.454111 | 289778 |
| NSC 174201 | 9393 | 9798 | 9595.5 | 286.3782464 | 300101 |
| NSC 409146 | 9586 | 11424 | 10505 | 1299.662264 | 349435 |
| NSC 601986 | 9413 | 11665 | 10539 | 1592.404471 | 353501 |
| NSC 640205 | 9133 | 11021 | 10077 | 1335.017603 | 368866 |
| NSC 668394 | 7055 | 16869 | 11962 | 6939.545951 | 381594 |
| NSC 97419 | 9266 | 15418 | 12342 | 4350.120918 | 61253 |
| doxorubicin | 2399 | 1489 | 1944 | 643.4671709 | 443939 |

The concentration of 50 µM was chosen because 50 µM of ciprofloxacin was used as the positive controls. Whether the fluorescence from some of these compounds in the library interfere with the assay was tested because previous HTS assays for DNA topoisomerase inhibitors were greatly interfered by certain compounds with strong fluorescence. The results demonstrated that fluorescence from these compounds per se did not interfere with the fluorescence signal from SYBR™ Green staining (FIG. 6 and Table 2).

The eight hits are seven quinolones (including levofloxacin, ciprofloxacin, oxolinic acid, enrofloxacin, norfloxacin, lomefloxacin, and nalidixic acid) and doxorubicin. Quinolones are known potent gyrase poisoning inhibitors. Interestingly, although nalidixic acid has an IC50 value much greater than 50 µM, the fluorescence intensity of the DNA samples in the presence of nalidixic acid was much lower comparing with the negative controls. In other words, this HTS assay can identify gyrase poisoning inhibitors even if they have a high IC50 against *E. coli* DNA gyrase.

Figure 7C:
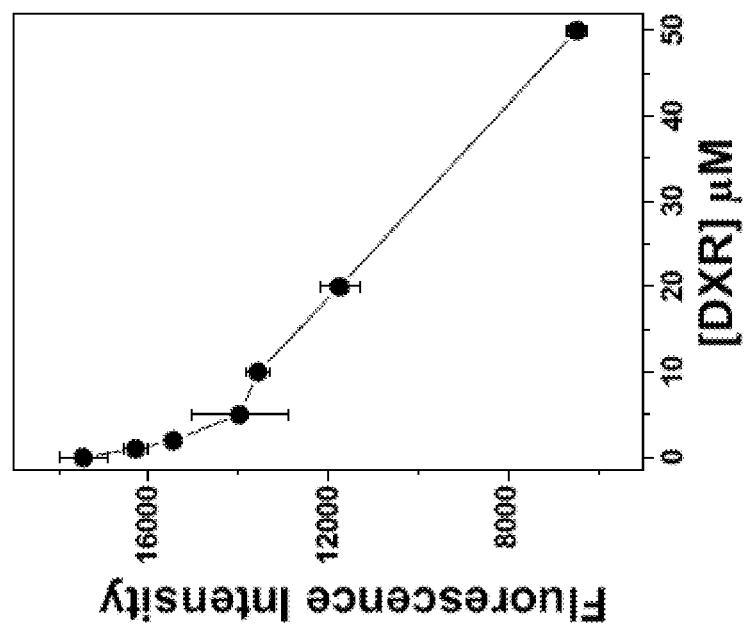

The only non-quinolone hit is doxorubicin, a DNA intercalator tightly binding to DNA. Agarose gel-based DNA cleavage assays showed that doxorubicin did not cause gyrase-mediated DNA cleavage and is not a gyrase poisoning inhibitor (FIG. 7). In other words, doxorubicin was a false positive. A possible reason is that the high affinity of doxorubicin for DNA resulted in the quenching of SYBR™ Green's fluorescence. The fluorescence-based DNA cleavage assay was repeated using 20 µM. Again, the fluorescence of SYBR™ Green was quenched (FIG. 7A). A doxorubicin titration experiment where different concentrations of doxorubicin were titrated into 200 ng of Rx pBR322 in 1 xgyrase DNA cleavage buffer was then performed. After the reaction mixtures were diluted 100 times, 1×SYBR™ Green was added. The results shown in FIG. 7C clearly demonstrated that doxorubicin quenched the fluorescence of SYBR™ Green.

In this HTS screen, several compounds, such as ethacridine, echinomycin, topotecan, and suramin, also caused significant low fluorescence signals to the DNA samples from the DNA cleavage assays at 50 µM. Nevertheless, at a final compound concentration of 20 µM, these compounds did not reduce the fluorescence intensity of SYBR™ Green, indicating that they are not gyrase poisoning inhibitors (FIG. 7A). Further validation through agarose gel-based DNA cleavage assays corroborated these findings, confirming that indeed, these compounds do not possess gyrase poisoning properties (FIG. 7B).

Example—3. Identify Inhibitors of Human DNA Topoisomerases

Figures 8A, 8B:
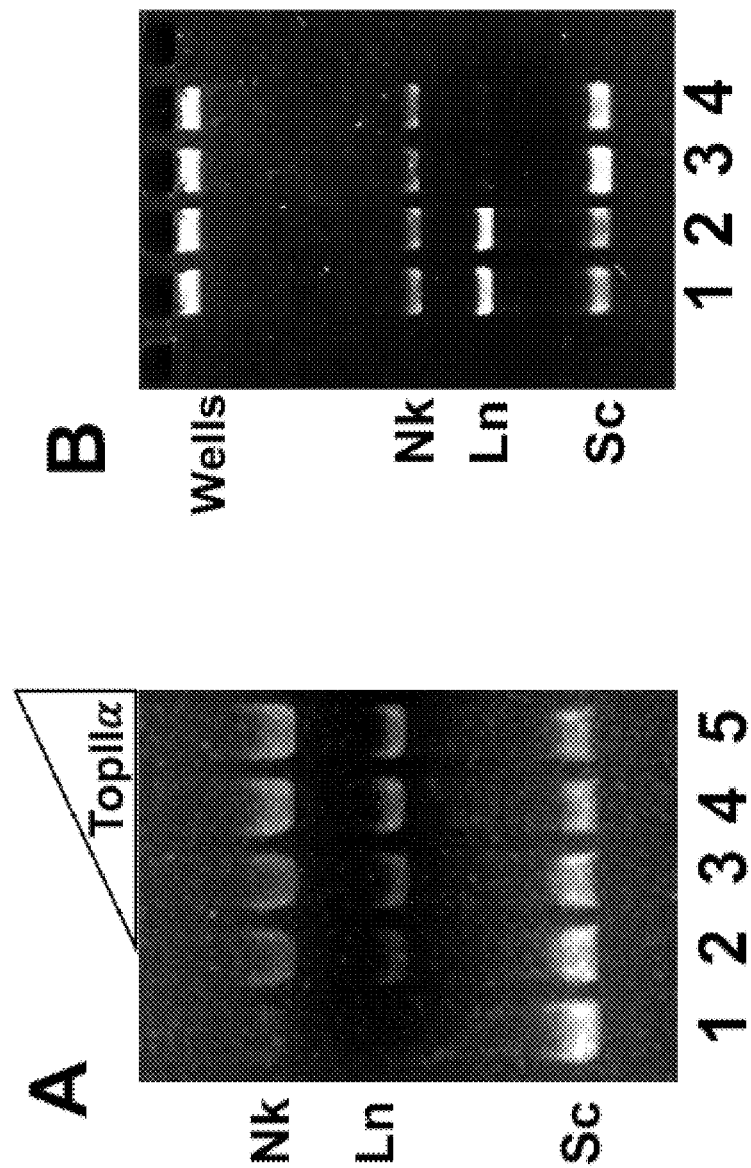
FIGS. 8A-8C. Human DNA TopoIIα mediated DNA cleavage assays, similar to the gyrase-mediated DNA cleavage assay, were performed as described in Materials and Methods. (A) and (B) Agarose gel-based DNA gyrase cleavage assays. (A) In the presence of 50 ELM etoposide, human TopoIIα mediated DNA cleavage products (the linear DNA and nicked DNA) are proportional to the amount of human TopoIIα used in the assay. Phenol extraction was used to purify DNA samples before the gel electrophoresis. Lanes 1-5 contain 0, 0.015, 0.03, 0.06, and 0.12 mg/mL of human TopoIIα, respectively. (B) Without phenol extraction, some DNA-protein complexes could not migrate from the wells into the gel. Lanes 1-4 are DNA samples from the assays in the presence (lanes 1 and 2) or absence (lanes 3 and 4) of 50 μM etoposide. 0.12 mg/mL of human TopoIIα was used for each assay. (C) Fluorescence intensity of the DNA samples in (B) after T5 exonuclease digestion and SYBR™ Green staining. Fluorescence intensity was measured using a Biotek microplate reader with excitation wavelength of 497 nm and emission wavelength of 525 nm.
Figure 8C:
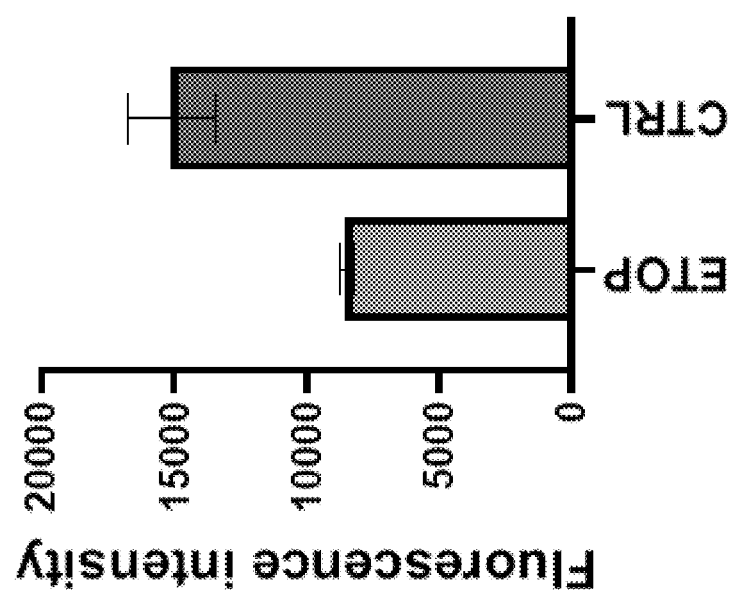

The possibility of establishing a similar DNA cleavage assay for human DNA topoisomerase IIα was also explored, as several anticancer drugs, such as etoposide and doxorubicin, act as poisoning inhibitors targeting this human DNA topoisomerase. The results are shown in FIG. 8. A titration experiment of human DNA topoisomerase IIα showed a progressive increase in the linear and nicked plasmid DNA products when using increasing concentrations of topoisomerase IIα in the presence of 50 µM of etoposide (FIG. 8A). Nevertheless, plasmid DNA cannot be all converted to linear or nicked form (FIG. 8). A possibility is that the IC50 of etoposide against human DNA topoisomerase IIα is much higher that 50 µM. Under this condition, not all plasmid DNA molecules was able to form topoisomerase IIα-DNA cleavage complexes and converted into linear or nicked form after SDS or sarkosyl trapped the cleavage complexes and proteinase K digested topoisomerase IIα. Without phenol extraction, certain DNA-protein complexes could not migrate into the agarose gel and were stuck in the wells (FIG. 8B). Nevertheless, a significant fluorescence difference of the DNA samples was observed between the presence and absence of etoposide (FIG. 8C). These results demonstrated the feasibility of establishing a similar fluorescence-based DNA cleavage assay for human DNA topoisomerase IIα.

In summary, the subject invention provides a novel fluorescence-based DNA cleavage assay to discover bacterial DNA gyrase poisoning inhibitors, based on the result/observation suggesting that multiple DNA gyrase molecules simultaneously bind to a plasmid DNA molecule to form multiple gyrase-DNA cleavage complexes on the same plasmid DNA molecule. These gyrase-DNA cleavage complexes, greatly stabilized by a DNA gyrase poisoning inhibitor, can be trapped by SDS or sarkosyl. Digestion of DNA gyrase by proteinase K result in the production of small DNA fragments. T5 exonuclease, which selectively digests linear and nicked DNA, can be used to completely digest the fragmented linear DNA molecules and, therefore, "amplify" the fluorescence signal of the DNA cleavage products after SYBR™ Green staining. This fluorescence-based DNA cleavage HTS assay was validated using a 50-coupound library. It has a Z prime value more than 0.5 and ready to screen different compound libraries. Similar fluorescence-based DNA cleavage assays may also be used to identify poisoning inhibitors against other DNA topoisomerases, such as human topoisomerase IIα.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting.

We claim:

1. A method for identifying an inhibitor targeting a DNA topoisomerase in a sample, the method comprising adding a circular double-stranded plasmid to the sample; adding the DNA topoisomerase; adding a detergent and a proteinase; adding an exonuclease; adding a DNA-staining dye; and determining the presence or absence of the inhibitor based on fluorescence in the sample.

2. The method of claim 1, wherein the DNA topoisomerase is a II DNA topoisomerases.

3. The method of claim 2, wherein the type II DNA topoisomerases is human DNA topoisomerase II, or DNA gyrase.

4. The method of claim 1, wherein the circular double-stranded plasmid has the ability to interconvert between a relaxed (rx) configuration and a supercoiled (sc) configuration.

5. The method of claim 1, wherein the detergent is sodium laureth sulfate (SLES), sodium dodecyl sulfate (SDS) and/or sarkosyl.

6. The method of claim 1, wherein the proteinase is proteinase K or a neutral, heat-sensitive serine protease (NHSSP).

7. The method of claim 1, wherein determining the presence or absence of the inhibitor based on the fluorescence in the sample comprises comparing the fluorescence with a control, wherein a lower fluorescence in the sample than a control is indicative of the presence of the inhibitor of the DNA topoisomerase, and wherein the control comprises the circular double-stranded plasmid in a supercoiled conformation.

8. The method of claim 1, wherein the exonuclease is T5 exonuclease (T5E).

9. The method of claim 1, further comprising adding ATP in the sample.

10. A method for determining whether a compound is an inhibitor targeting a DNA topoisomerase, the method comprising mixing the compound with a circular double-stranded plasmid and the DNA topoisomerase; adding a detergent and a proteinase to the mixture, adding an exonuclease to the mixture; adding a DNA-staining dye; and determining whether the compound is an inhibitor targeting the DNA topoisomerase based on fluorescence of the mixture.

11. The method of claim 10, wherein the DNA topoisomerase is a type II DNA topoisomerases.

12. The method of claim 11, wherein the type II DNA topoisomerases is human DNA topoisomerase II, or DNA gyrase.

13. The method of claim 10, wherein the circular double-stranded plasmid has the ability to interconvert between a relaxed (rx) configuration and a supercoiled (sc) configuration.

14. The method of claim 10, wherein the detergent is being-SLES, SDS and/or sarkosyl.

15. The method of claim 10, wherein the proteinase is proteinase K or NHSSP.

16. The method of claim 10, wherein determining whether the compound is an inhibitor based on the fluorescence comprises comparing the fluorescence with a control, wherein a lower fluorescence in the mixture than the control indicates that the compound is an inhibitor of the DNA topoisomerase, wherein a higher or comparable fluorescence in the mixture than the control indicates that the compound is not an inhibitor of the DNA topoisomerase, and wherein the control comprises the circular double-stranded plasmid in a supercoiled conformation.

17. The method of claim 10, wherein the exonuclease is T5E.

18. The method of claim 10, further comprising adding ATP in the mixture.

* * * * *